United States Patent
Okada

(10) Patent No.: US 7,063,661 B2
(45) Date of Patent: Jun. 20, 2006

(54) ENDOSCOPIC MUCOUS MEMBRANE RESECTION INSTRUMENT AND ENDOSCOPIC MUCOUS MEMBRANE RESECTION METHOD

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 171 days.

(21) Appl. No.: 10/764,893

(22) Filed: Jan. 26, 2004

(65) Prior Publication Data

US 2004/0158127 A1   Aug. 12, 2004

(30) Foreign Application Priority Data

Jan. 31, 2003 (JP) .............................. 2003-024896

(51) Int. Cl.
*A61B 1/04* (2006.01)

(52) U.S. Cl. ............... 600/127; 600/104; 600/106; 600/107; 600/129; 606/46; 606/47; 606/113; 606/170

(58) Field of Classification Search ........ 600/104–107, 600/127, 129; 606/1, 113, 170, 205, 46, 606/47
See application file for complete search history.

(56) References Cited

U.S. PATENT DOCUMENTS

| 6,071,233 | A  | * | 6/2000 | Ishikawa et al. ............. 600/104 |
| 6,352,503 | B1 | * | 3/2002 | Matsui et al. ................ 600/104 |
| 6,527,753 | B1 | * | 3/2003 | Sekine et al. ................ 604/264 |
| 2001/0053909 | A1 | | 12/2001 | Nakada et al. |
| 2004/0225183 | A1 | * | 11/2004 | Michlitsch et al. ......... 600/106 |

FOREIGN PATENT DOCUMENTS

| JP | 6-75402 | 10/1994 |
| JP | 9-187415 | 7/1997 |
| JP | 2001-275933 | 10/2001 |
| JP | 2002-45369 | 2/2002 |

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

One of a first endoscopic treatment instrument setting state and a second endoscopic treatment instrument setting state is selectable. In the former state, when a first diathermic snare is removably inserted in a flexible tube, a loop portion is circumferentially broadened and disposed along a first projection portion. In the latter state, when a second diathermic snare is removably inserted in the flexible tube, a loop portion is circumferentially broadened and disposed along a second projection portion.

9 Claims, 25 Drawing Sheets

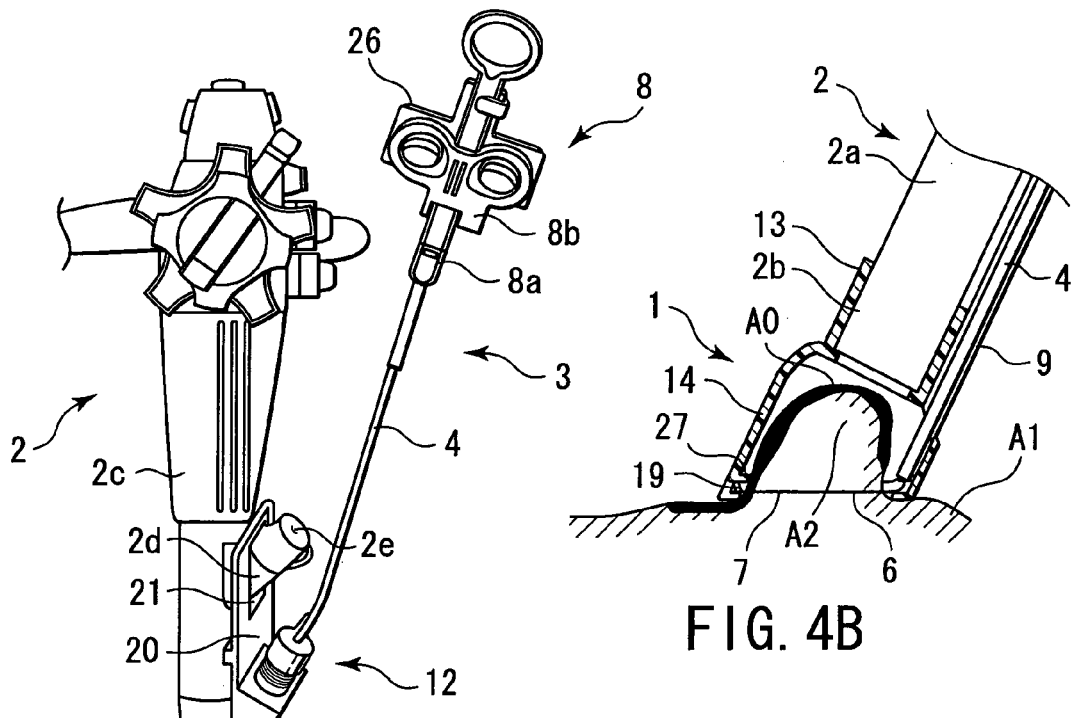
FIG. 4A
FIG. 4B
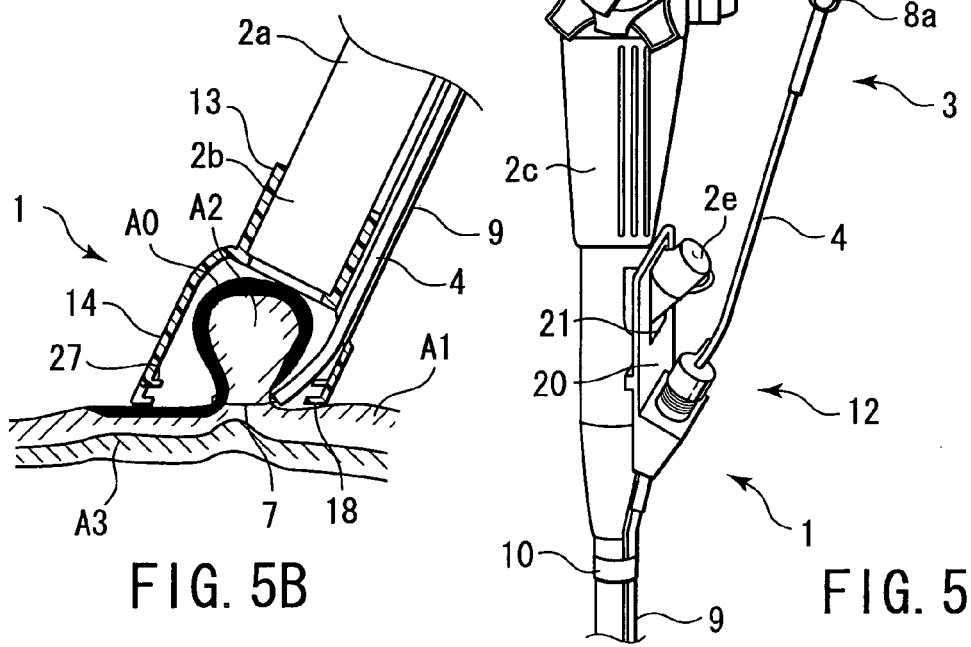
FIG. 5B
FIG. 5A

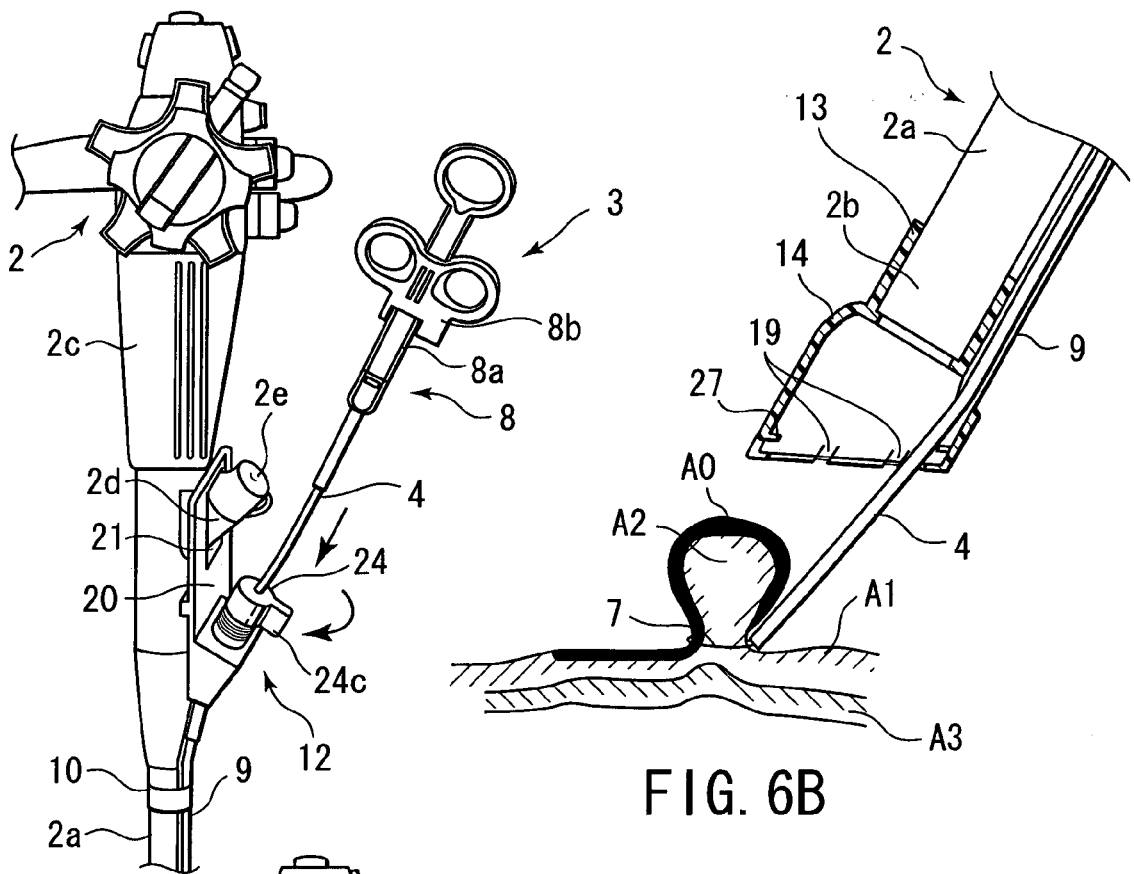
FIG. 6A
FIG. 6B
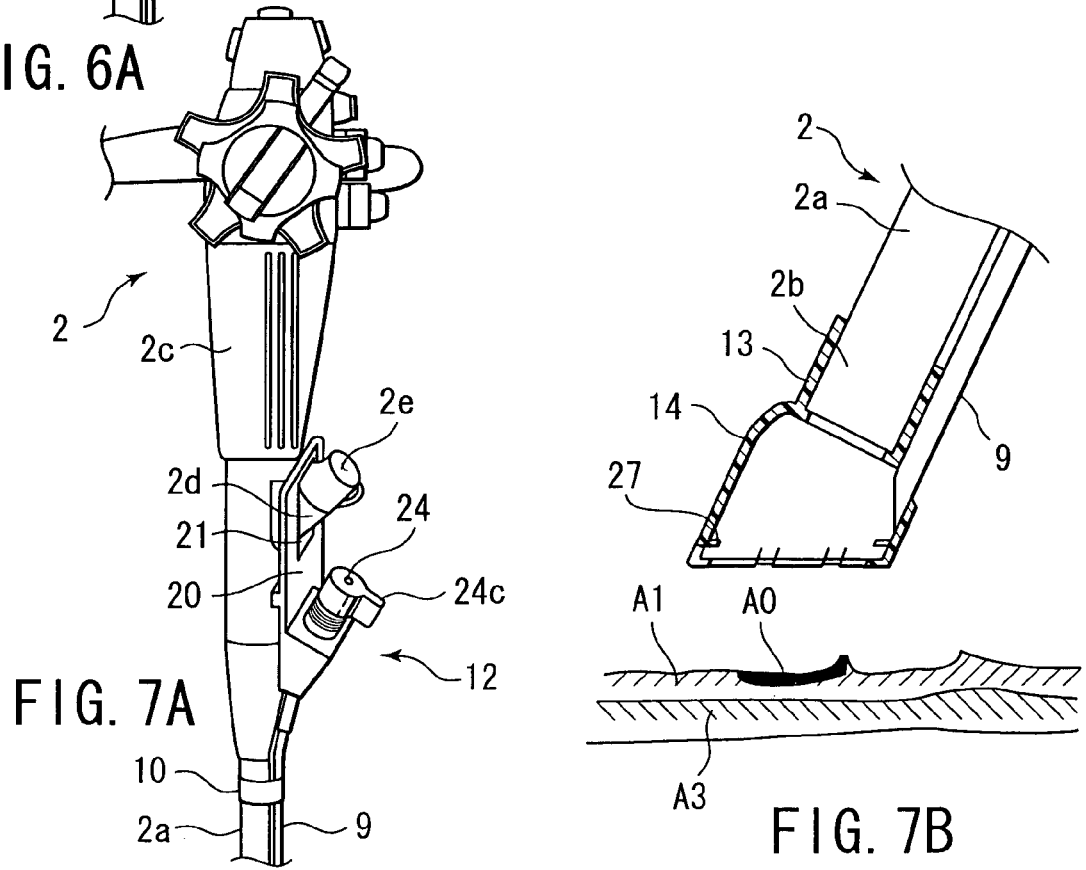
FIG. 7A
FIG. 7B

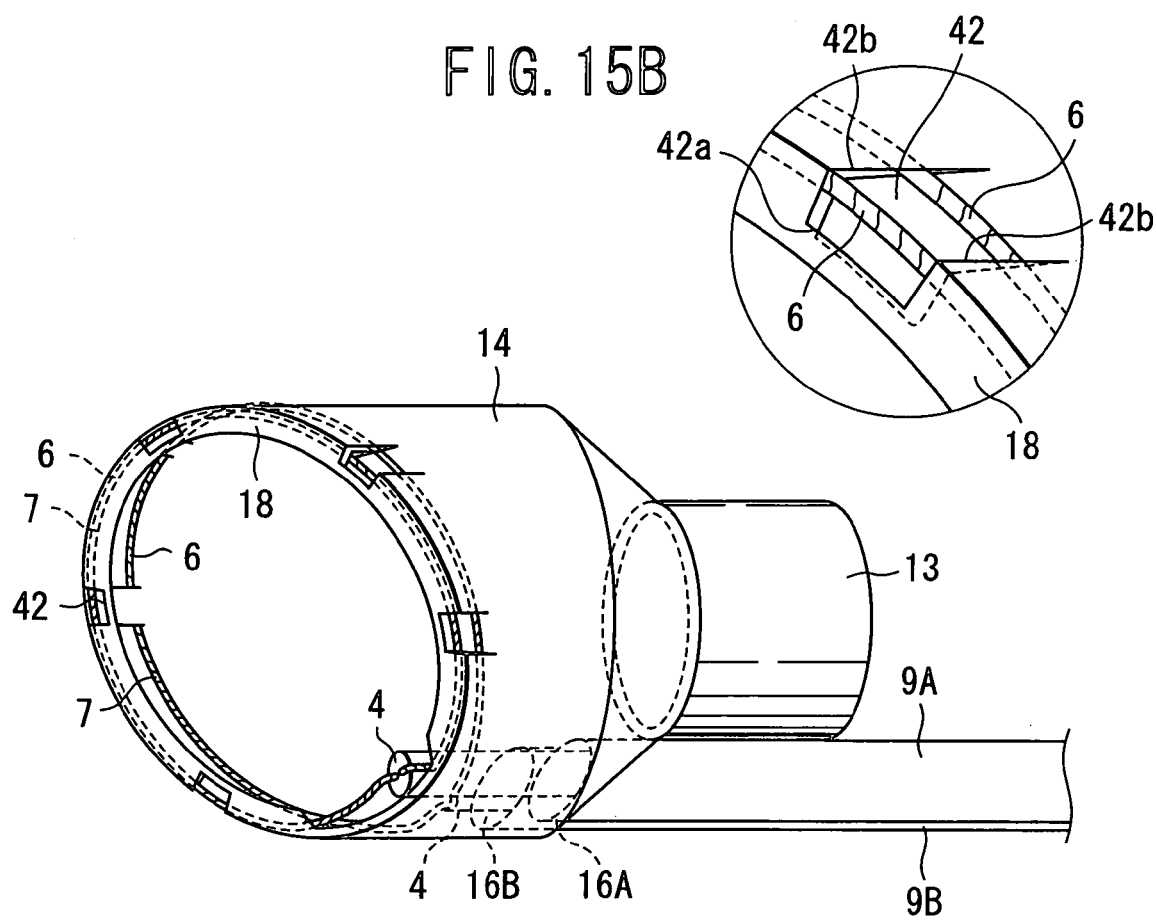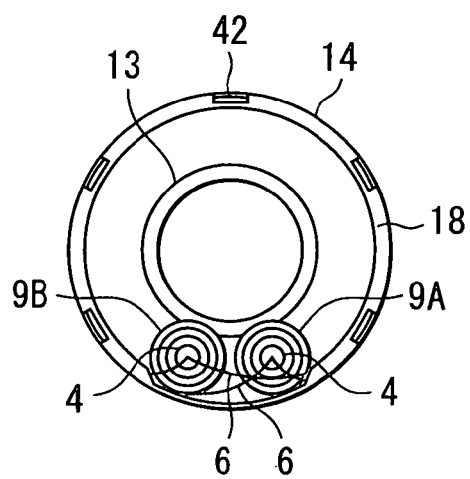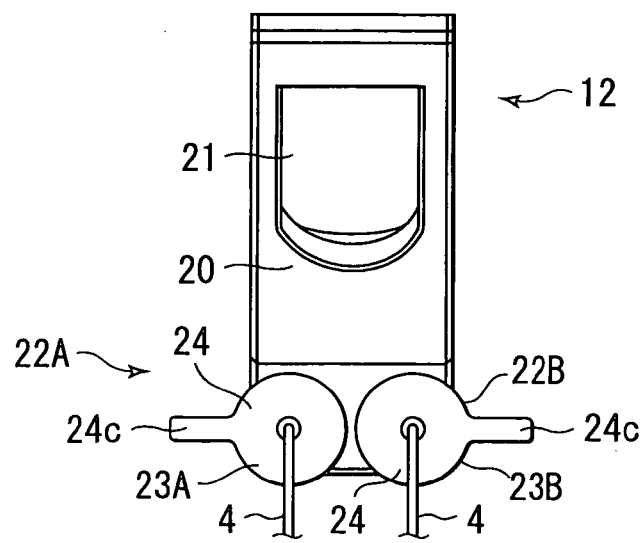

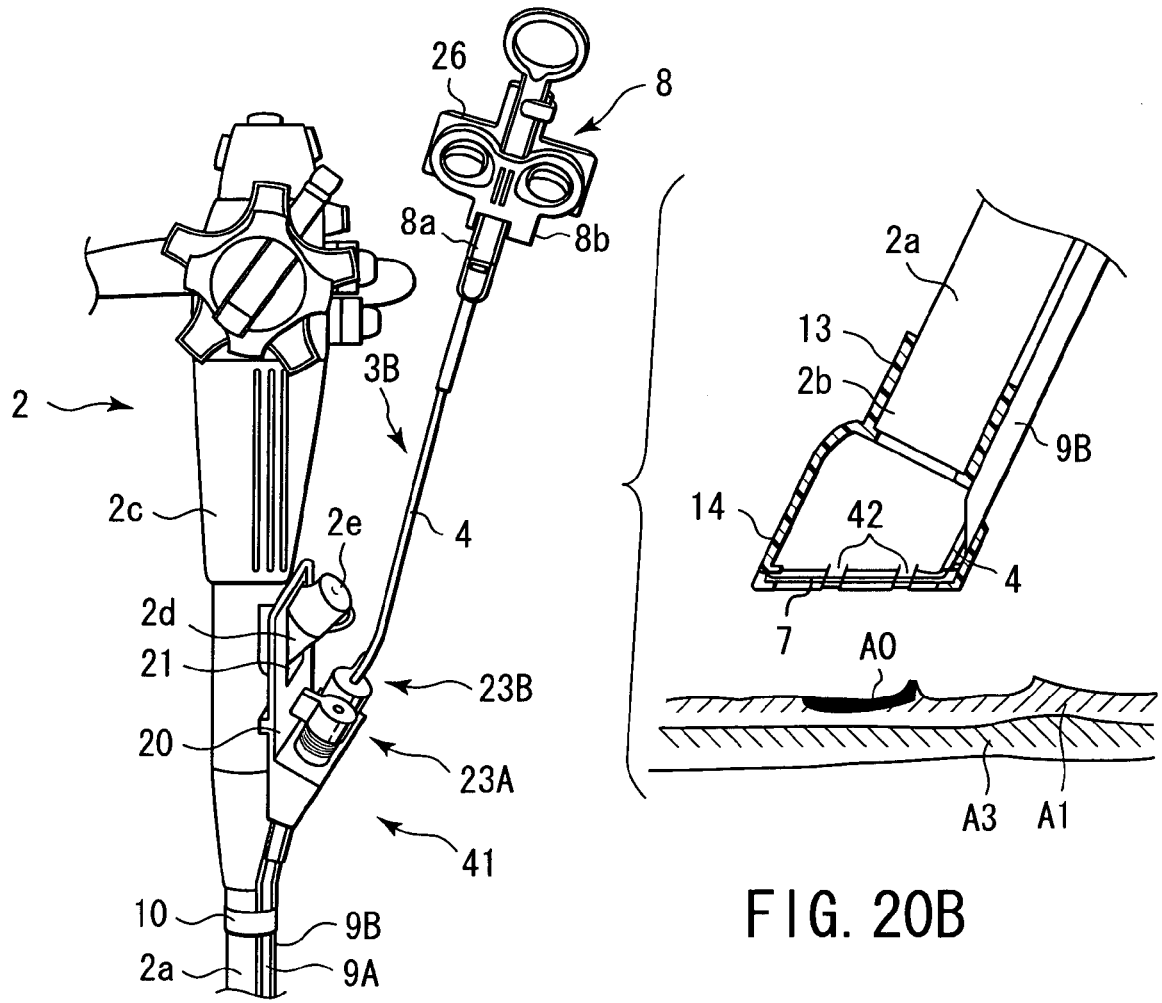
FIG. 20A
FIG. 20B
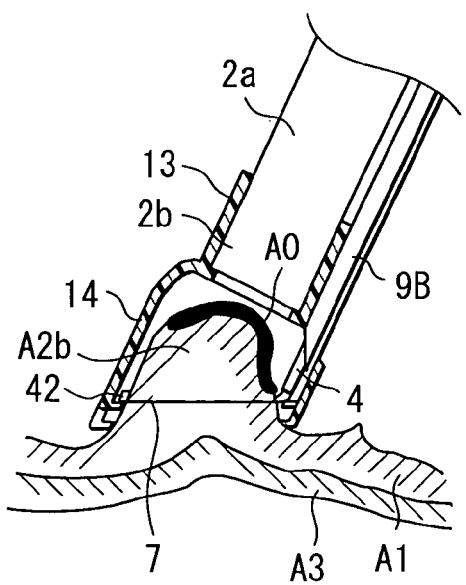
FIG. 20C

ENDOSCOPIC MUCOUS MEMBRANE RESECTION INSTRUMENT AND ENDOSCOPIC MUCOUS MEMBRANE RESECTION METHOD

CROSS-REFERENCE TO RELATED APPLICATIONS

This application is based upon and claims the benefit of priority from the prior Japanese Patent Application No. 2003-024896, filed Jan. 31, 2003, the entire contents of which are incorporated herein by reference.

BACKGROUND OF THE INVENTION

1. Field of the Invention

The present invention relates to a mucous membrane resection instrument for use in an endoscope (hereinafter referred to as "endoscopic mucous membrane resection instrument"), which sucks a mucous membrane in a substantially cylindrical cap attached to a distal end of an insertion portion of an endoscope, thereby forming a polyp-like projection portion, and resects a proximal portion of the projection portion using a diathermic snare, and to a method for the mucous membrane resection.

2. Description of the Related Art

In recent years, endoscopic mucous membrane resection for resecting a mucous membrane of a target part is performed using an endoscope without ventrotomy, thereby treating an early cancer at the esophagus or stomach. Jpn. U.M. Appln. KOKAI Publication No. 6-75402 (Patent Document 1) and Jpn. Pat. Appln. KOKAI Publication No. 2001-275933 (Patent Document 2) disclose methods wherein an endoscope and a diathermic snare are used in combination. In these methods, a substantially cylindrical hood is attached to a distal end of an insertion section of the endoscope. A flange-like projection (claw portion), which protrudes inward, is provided on the inner peripheral surface of the distal end portion of the hood.

Further, the diathermic snare includes a flexible sheath, an operation wire, and a snare wire. The operation wire is inserted in the flexible sheath so as to be advanceable and retreatable. The snare wire is coupled to the distal end of the operation wire. The snare wire is received in the sheath so as to be advanceable and retreatable. The snare wire has a loop portion that is broadened in a substantially circular or oval loop shape when the snare wire is advanced from the sheath.

When the diathermic snare is used, it is inserted in the channel in the endoscope. The diathermic snare is extended through the channel of the endoscope to the distal end side of the endoscope, and the diathermic snare is projected forward from the channel of the endoscope. Then, a work is conducted to set the loop portion of the diathermic snare in the state in which the loop portion is disposed along the flange-like projection portion on the inside of the hood (hereinafter this work being referred to as "looping work"). In this state, a target mucous membrane to be resected is sucked in the hood. At this time, the mucous membrane sucked in the hood is swollen in a hemispherical polyp shape. A proximal end portion of the swollen part of the mucous membrane sucked in the hood is strangulated by the diathermic snare and resected with electric power supplied to the snare.

Jpn. Pat. Appln. KOKAI Publication No. 2002-45369 (Patent Document 3) discloses a hood for an endoscope. A cap section is detachably attached to a distal end portion of the endoscope. A flexible tube for introducing a treatment instrument is provided along an insertion portion of the endoscope. A distal end portion of the flexible tube is coupled to the cap section. A diathermic snare is inserted in advance in the flexible tube. A loop portion of the diathermic snare is fixed to a projection portion within the cap section by an adhesive.

In the treatment instruments of Patent Document 1 and Patent Document 2, the hood along with the endoscope is inserted in the body cavity in advance. In this state, the diathermic snare is inserted in the channel in the endoscope, and a work for disposing the loop portion of the diathermic snare within the cap section of the hood (hereinafter referred to as "looping work") is performed.

In the technique of Patent Document 3, the loop portion of the diathermic snare is fixed in advance to the projection portion within the cap section by means of an adhesive. This makes it possible to omit the time-consuming looping work during the treatment for endoscopic mucous membrane resection. However, in the case of performing endoscopic mucous membrane resection, when a target to-be-resected mucous membrane is large, it is not possible to suck the entire target mucous membrane into the cap section of the hood at a time. To cope with this problem, the large target part is divided into a plurality of portions and the divided portions are resected (hereinafter referred to as "divisional resection"). In the case of performing the divisional resection of the large target part, the same treatment procedure (the aforementioned endoscopic mucous membrane resection) is repeated several times.

BRIEF SUMMARY OF THE INVENTION

In order to solve the above-described problem, the present invention may provide an endoscopic mucous membrane resection instrument included, a transparent cap section detachably attached to a distal end portion of an endoscope, the cap section including a cylindrical body having a substantially circular shape, a flange-like first projection portion projecting inward from the cylindrical body in a vicinity of a distal end edge of the cylindrical body, and a second projection portion that projects inward and is provided on an inner peripheral surface of the cylindrical body at a position spaced apart from the first projection portion, a flexible tube having a distal end portion and a proximal end portion, the tube being extended along an insertion section of the endoscope and the distal end portion of the tube being fixed in a state in which the distal end portion of the tube communicates with the cap section, when the cap section is attached to the endoscope, a first endoscopic treatment instrument for a mucous membrane resection work, which has an insertion section to be removably inserted in the tube, the treatment instrument having a first loop portion for mucous membrane resection at a distal end portion of the insertion section thereof, the first loop portion being broadened and disposed along an inner peripheral surface of the cylindrical body in a state in which the first loop portion is engaged with the first projection portion, when the insertion section of the first endoscopic treatment instrument is inserted in the tube, and a second endoscopic treatment instrument having an insertion section to be removably inserted in the tube, the second endoscopic treatment instrument being inserted in the tube after a first mucous membrane resection work by the first endoscopic treatment instrument, thereby performing a second mucous membrane resection work, the treatment instrument having a second loop portion for mucous membrane resection at a distal end portion of the insertion section thereof, the second loop portion being broadened and disposed along the inner peripheral surface of the cylindrical body in a state in which the second loop portion is engaged with the second projection portion, when the insertion section of the second endoscopic treatment instrument is inserted in the tube.

Preferably, each of the first endoscopic treatment instrument and the second endoscopic treatment instrument is a diathermic snare in which each of the first and second loop portion is formed of a snare wire.

The present invention may provide an endoscopic mucous membrane resection instrument included, a transparent cap section detachably attached to a distal end portion of an endoscope, the cap section including a cylindrical body having a substantially circular shape, and a flange-like projection portion projecting inward from the cylindrical body in a vicinity of a distal end edge of the cylindrical body, a plurality of flexible tubes for insertion of treatment instruments, each of the tubes having a distal end portion and a proximal end portion, each of the tubes being extended along an insertion section of the endoscope and the distal end portion of the tube being fixed in a state in which the distal end portion of the tube communicates with the cap section, when the cap section is attached to the endoscope, a first endoscopic treatment instrument for a mucous membrane resection work, which has an insertion section to be removably inserted in one of the tubes, the treatment instrument having a first loop portion for mucous membrane resection at a distal end portion of the insertion section thereof, the first loop portion being broadened and disposed along the inner peripheral surface of the cylindrical body in a state in which the first loop portion is engaged with the projection portion, when the insertion section of the first endoscopic treatment instrument is inserted in the tube, and a second endoscopic treatment instrument having an insertion section to be removably inserted in the tube other than the tube in which the first endoscopic treatment instrument is inserted, the treatment instrument having a second loop portion for mucous membrane resection at a distal end portion of the insertion section thereof, the second loop portion being broadened and disposed along the inner peripheral surface of the cylindrical body in a state in which the second loop portion is engaged with the projection portion, when the insertion section of the second endoscopic treatment instrument is inserted in the tube.

Preferably, each of the first endoscopic treatment instrument and the second endoscopic treatment instrument is a diathermic snare in which each of the first and second loop portion is formed of a snare wire.

The present invention may provide an endoscopic mucous membrane resection instrument included, a transparent cap section detachably attached to a distal end portion of an endoscope, the cap section including a cylindrical body having a substantially circular shape, a flange-like first projection portion projecting inward from the cylindrical body in a vicinity of a distal end edge of the cylindrical body, and a second projection portion that projects inward and is provided on an inner peripheral surface of the cylindrical body at a position spaced apart from the first projection portion, two flexible tubes for insertion of treatment instruments, each of the tubes having a distal end portion and a proximal end portion, each of the tubes being extended along an insertion section of the endoscope and the distal end portion of the tube being fixed in a state in which the distal end portion of the tube communicates with the cap section, when the cap section is attached to the endoscope, first and second endoscopic treatment instruments having insertion sections to be removably inserted in the tubes respectively, each of the treatment instruments having a loop portion at a distal end portion of the insertion section thereof, the loop portion being broadened and disposed along the inner peripheral surface of the cylindrical body in a state in which the loop portion is engaged with one of the first projection portion and the second projection portion, when the insertion sections of the first and second endoscopic treatment instruments are inserted in the tubes, and treatment instrument setting means for setting at the same time a first endoscopic treatment instrument setting state in which the loop portion of the first endoscopic treatment instrument removably inserted in one of the tubes is broadened and disposed on an inner peripheral surface of the cylindrical body in a state in which the loop portion of the first endoscopic treatment instrument is engaged with the first projection portion, and a second endoscopic treatment instrument setting state in which the loop portion of the second endoscopic treatment instrument removably inserted in the other tube is broadened and disposed on the inner peripheral surface of the cylindrical body in a state in which the loop portion of the second endoscopic treatment instrument is engaged with the second projection portion.

Preferably, the first endoscopic treatment instrument includes a ligator in which the loop portion is formed of a ligation loop capable of tightly binding and ligating a living tissue, and the second endoscopic treatment instrument is a diathermic snare in which the loop portion is formed of a snare wire.

The present invention may provide an endoscopic mucous membrane resection method included, a resection instrument setting step of fitting an endoscopic mucous membrane resection instrument on a distal end portion of an insertion section of an endoscope, the endoscopic mucous membrane resection instrument being set in a state in which a first diathermic snare is preset in a cap section such that a loop portion of the first diathermic snare is engaged on a first projection portion formed at a distal end portion of the cap section and the loop portion is broadened along an inner peripheral surface of the cap section, a step of inserting the endoscope and the resection instrument into a body cavity and moving a distal opening portion of the cap section toward a target to-be-resected mucous membrane, a step of causing a suction force to act within the cap section in a state in which the distal opening portion of the cap section is pushed on the mucous membrane, thereby sucking and raising a to-be-resected part of the mucous membrane within the cap section by a negative pressure, a step of reducing a size of the loop portion of a snare wire of the first diathermic snare by operating the first diathermic snare, thereby tightly binding a proximal portion of a raised part of the mucous membrane, a first mucous membrane resection work step of causing a high-frequency current to flow in the snare wire while strangulating the proximal portion of the raised part by the loop portion of the snare wire, thereby resecting the to-be-resected part of the mucous membrane, a step of removing the first diathermic snare used in the preceding steps from the resection instrument after the completion of the first mucous membrane resection work, and a second resection work step of resecting a remaining part of the mucous membrane, which is not resected by the first resection work, the second resection work step including, a step of moving the distal opening portion of the cap section toward a second to-be-resected part of the target mucous membrane in a state in which the first diathermic snare is not set in the resection instrument, a step of causing a suction force to act within the cap section in a state in which the distal opening portion of the cap section is pushed on the second to-be-resected part of the mucous membrane, thereby sucking and raising the second to-be-resected part of the mucous membrane within the cap section by a negative pressure, a step of broadening a loop portion of a second diathermic snare along an inner peripheral surface of the cap section and disposing the loop portion on a second projection portion which projects inward and is provided at a position spaced apart from the first projection portion, a step of largely raising the second to-be-resected part of the mucous membrane by sucking the second to-be-resected part more strongly than before insertion of the second diathermic snare, a step of reducing a size of the loop portion of a snare wire of the second diathermic snare by operating the second diathermic snare, thereby tightly binding a proximal portion of the second to-be-resected part of the mucous membrane, a second resection work step of causing, like the first resection work, a high-frequency current to flow in the snare wire while strangulating the proximal portion of the to-be-resected part by the loop portion of the snare wire, thereby resecting the remaining to-be-resected part, and a recovery step of recovering, after the completion of the second resection work, the resected part of the mucous membrane resected by the second resection work and the resected part of the mucous membrane resected by the first resection work in the state in which both the resected parts are sucked and held in the cap section, by taking out both the resected parts from the body cavity along with the endoscope.

The present invention may provide an endoscopic mucous membrane resection method included, a resection instrument setting step of fitting an endoscopic mucous membrane resection instrument on a distal end portion of an insertion section of an endoscope, the endoscopic mucous membrane resection instrument being set in a state in which two diathermic snares are preset in a cap section such that loop portions of the two diathermic snares are engaged on a projection portion formed at a distal end portion of the cap section and the loop portions are broadened along an inner peripheral surface of the cap section, a step of inserting the endoscope and the resection instrument into a body cavity and moving a distal opening portion of the cap section toward a target to-be-resected mucous membrane, a step of causing a suction force to act within the cap section in a state in which the distal opening portion of the cap section is pushed on the mucous membrane, thereby sucking and raising a to-be-resected part of the mucous membrane within the cap section by a negative pressure, a step of reducing a size of the loop portion of a snare wire of one of the diathermic snares by operating said one of the diathermic snares, thereby tightly binding a proximal portion of a raised part of the mucous membrane, a first mucous membrane resection work step of causing a high-frequency current to flow in the snare wire while strangulating the proximal portion of the raised part by the loop portion of the snare wire, thereby resecting the to-be-resected part of the mucous membrane, a step of removing the diathermic snare used in the preceding steps from the resection instrument after the completion of the first mucous membrane resection work, and a second resection work step of resecting a remaining part of the mucous membrane, which is not resected by the first resection work, the second resection work step including, a step of moving the distal opening portion of the cap section toward a second to-be-resected part of the target mucous membrane, a step of causing a suction force to act within the cap section in a state in which the distal opening portion of the cap section is pushed on the second to-be-resected part of the mucous membrane, thereby sucking and raising the second to-be-resected part of the mucous membrane within the cap section by a negative pressure, a step of tightly binding a proximal portion of a raised part of the mucous membrane by the loop portion of the snare wire by operating the diathermic snare other than the diathermic snare used in the first resection work, a second resection work step of causing a high-frequency current to flow in the snare wire while strangulating the proximal portion of the raised part by the loop portion of the snare wire, thereby resecting the remaining to-be-resected part, and a recovery step of recovering, after the completion of the second resection work, the resected part of the mucous membrane resected by the second resection work and the resected part of the mucous membrane resected by the first resection work in the state in which both the resected parts are sucked and held in the cap section, by taking out both the resected parts from the body cavity along with the endoscope.

The present invention may provide an endoscopic mucous membrane resection method included, a resection instrument setting step of fitting an endoscopic mucous membrane resection instrument on a distal end portion of an insertion section of an endoscope, the endoscopic mucous membrane resection instrument including a transparent cap section detachably attached to the distal end portion of the endoscope, one diathermic snare and one ligator, the endoscopic mucous membrane resection instrument being set in a state in which a loop portion of the ligator is engaged in advance on a first projection portion formed at a distal end portion of the cap section and the loop portion is broadened along an inner peripheral surface of the cap section, and also set in a state in which a loop portion of the diathermic snare is engaged on a second projection portion projecting inward at a position spaced apart from the first projection portion and the loop portion is broadened along the inner peripheral surface of the cap section, a step of inserting the endoscope and the resection instrument into a body cavity and moving a distal opening portion of the cap section toward a target to-be-resected mucous membrane, a step of causing a suction force to act within the cap section in a state in which the distal opening portion of the cap section is pushed on the mucous membrane, thereby sucking and raising a to-be-resected part of the mucous membrane within the cap section by a negative pressure, a step of reducing a size of the loop portion of a ligation loop by operating the ligator, thereby tightly binding a proximal portion of a raised part of the mucous membrane, a step of releasing the ligation loop and keeping a state in which the proximal portion of the raised part of the mucous membrane is tightly bound by the ligation loop, a step of sucking in the cap section the raised part of the mucous membrane tightly bound by the ligation loop, a step of reducing a size of the loop portion of a snare wire by operating the diathermic snare, thereby tightly binding an upper-side portion of the raised part of the mucous membrane that is already tightly bound by the ligation loop, a resection work step of causing a high-frequency current to flow in the snare wire while strangulating the upper-side portion of the raised part of the mucous membrane by the loop portion of the snare wire, thereby resecting the to-be-resected part of the mucous membrane, and a recovery step of recovering, after the completion of the resection work, the resected part of the mucous membrane resected by the resection work in a state in which the resected part is sucked and held in the cap section, by taking out the resected part from the body cavity along with the endoscope.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL
VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4A is a perspective view showing a fixed state of the proximal-side coupling section of the endoscopic mucous membrane resection instrument according to the first embodiment;

FIG. 4B is a vertical cross-sectional view of a main part, showing the state in which a target to-be-resected mucous membrane part is raised;

FIG. 5A is a perspective view showing the state in which a restriction member is removed from an operation section of a first diathermic snare of the endoscopic mucous membrane resection instrument according to the first embodiment;

FIG. 5B is a vertical cross-sectional view of the main part, showing the state in which a loop portion of a snare wire is reduced to tightly bind a proximal portion of the target mucous membrane part;

FIG. 6A is a perspective view showing the state in which the engagement of a sheath of the first diathermic snare of the endoscopic mucous membrane resection instrument according to the first embodiment is released;

FIG. 6B is a vertical cross-sectional view of the main part, showing the state in which the distal end portion of the sheath is projected from the cap section;

FIG. 7A is a perspective view showing the state in which the first diathermic snare is removed from the endoscopic mucous membrane resection instrument according to the first embodiment;

FIG. 7B is a vertical cross-sectional view of the main part, showing the state in which only a portion of the target part is resected;

FIG. 15A is a perspective view of the main part, showing the state in which the two diathermic snares are set in the cap section of the endoscopic mucous membrane resection instrument according to the second embodiment;

FIG. 15B is a perspective view showing the state in which an encircled part in FIG. 15A is enlarged;

FIG. 16A is a front view of the main part, showing the state in which two flexible tubes are juxtaposed outside the endoscope attachment section of the endoscopic mucous membrane resection instrument according to the second embodiment;

FIG. 16B is a front view of the main part, showing the state in which two treatment instrument insertion sections are laterally juxtaposed at an end portion of the hook member of the proximal-side coupling section;

FIG. 20A is a perspective view showing the state in which the first diathermic snare is removed from the endoscopic mucous membrane resection instrument according to the second embodiment;

FIG. 20B is a vertical cross-sectional view of the main part, showing the state in which only a portion of the target part is resected; FIG. 20C is a vertical cross-sectional view of the main part, showing the state in which a second to-be-resected portion of the mucous membrane is sucked in the cap section;

DETAILED DESCRIPTION OF THE INVENTION

Figures 1A, 1B:
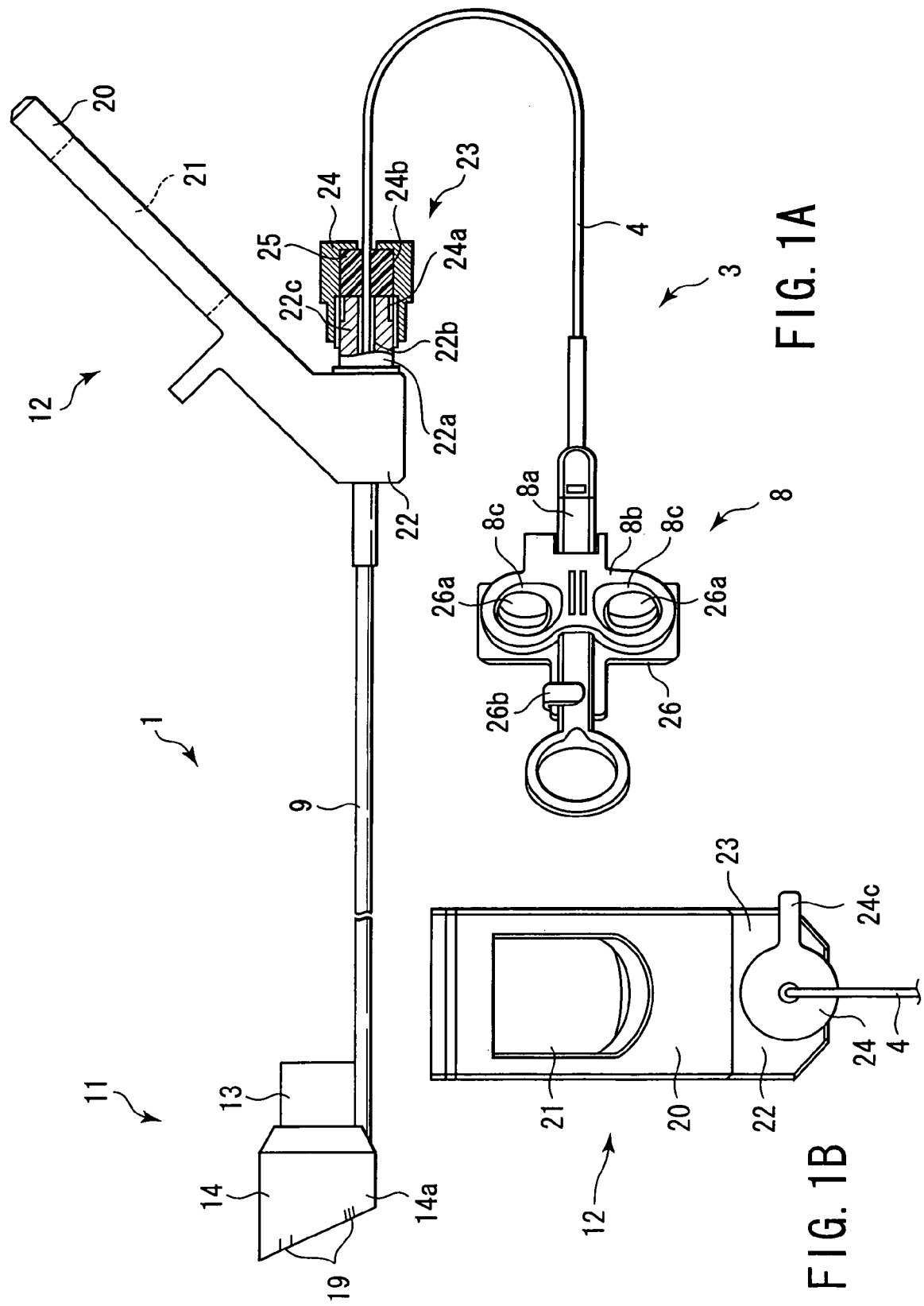
FIG. 1A is a side view showing an endoscopic mucous membrane resection instruction according to a first embodiment of the present invention.
FIG. 1B is a front view showing a proximal-side coupling section of the endoscopic mucous membrane resection instruction.

A first embodiment of the present invention will now be described with reference to FIGS. 1A through 12B. FIG. 1A shows a mucous membrane resection instrument 1 for use in an endoscope (hereinafter referred to as "endoscopic mucous membrane resection instrument 1") according to the embodiment of the invention. As is shown in FIGS. 4A and 4B, the resection instrument 1 is used in combination with an endoscope 2 and two diathermic (high-frequency) snares 3 and 31 serving as endoscopic treatment instruments. The two diathermic snares 3 and 31 have the same structure.

The endoscope 2 is provided with an elongated insertion section 2a to be inserted in the body. The insertion section 2a has a distal end portion 2b at its distal end. The distal end portion 2b is equipped with an observation optical system, an illumination optical system and a distal opening portion of a treatment instrument insertion channel, although these elements are not shown. Further, a proximal end portion of the insertion section 2a is provided with a proximal-side operation section 2c. The operation section 2c is provided with a treatment instrument insertion section 2d in a projecting fashion. The treatment instrument insertion section 2d is coupled to a proximal-side opening portion of the treatment instruction insertion channel. The treatment instrument insertion section 2d is furnished with a forceps cap 2e.

Figure 2:
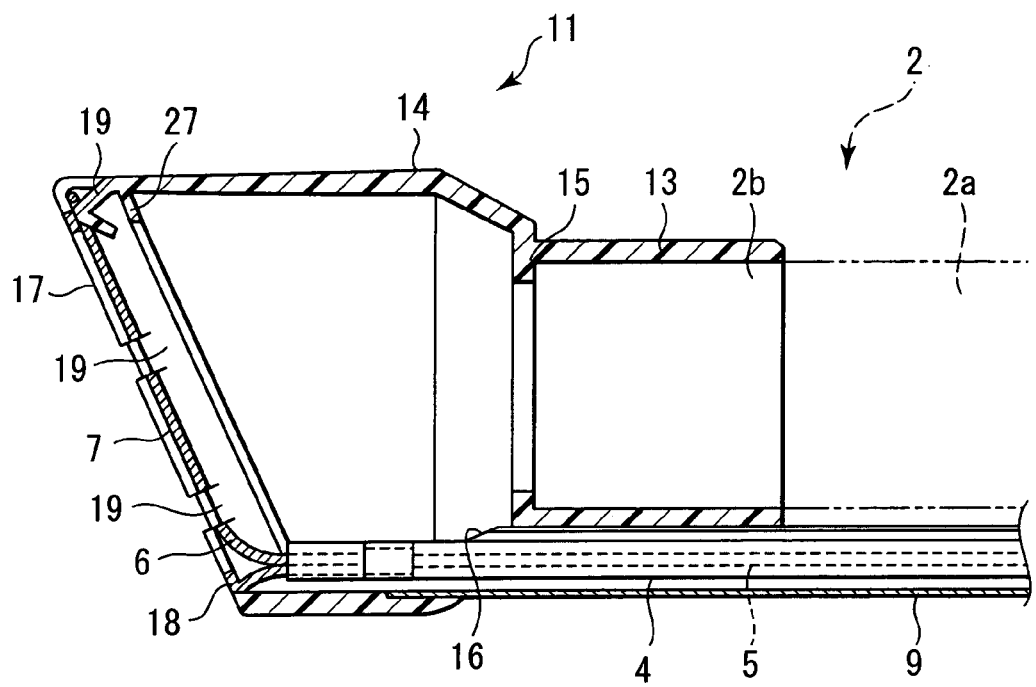
FIG. 2 is a vertical cross-sectional view showing a distal-side coupling section of the endoscopic mucous membrane resection instruction according to the first embodiment.

The diathermic snare 3 is provided with an elongated flexible sheath 4 having electrical insulation properties. As is shown in FIG. 2, an operation wire 5 is inserted in the flexible sheath 4 so as to be advanceable/retreatable. A distal end portion of the operation wire 5 is connected to a snare wire 6. A substantially oval loop portion 7 is formed at the snare wire 6.

A proximal end portion of the flexible sheath 4 is provided with an operation section 8. The operation section 8 includes a shaft-shaped guide member 8a and a slider 8b that is axially movable along the guide member 8a. The guide member 8a is coupled to a proximal end portion of the flexible sheath 4. Further, a wire insertion hole (not shown) for insertion of the operation wire 5 is formed in the guide member 8a.

The slider 8b has a pair of finger hook portions 8c. A proximal end portion of the operation wire 5 is connected to the slider 8b. The slider 8b is axially advanced/retreated along the guide member 8a. With the sliding operation of the slider 8b, the operation wire 5 is axially advanced/retreated. Thereby, the loop portion 7 of the snare wire 6 is projected/retreated from/in the distal end portion of the flexible sheath 4. When the slider 8b is operated, if the slider 8b is advanced relative to the guide member 8a, the loop portion 7 is projected from the flexible sheath 4 and is broadened in a substantially oval shape by its own self-opening capability. On the other hand, if the slider 8b is retreated relative to the guide member 8a, the loop portion 7 is reduced and retreated into the flexible sheath 4.

As is shown in FIG. 2, the resection instrument 1 is provided with an elongated flexible tube 9 that is externally attached along the insertion section 2a of the endoscope 2. The length of the tube 9 is set to be substantially equal to, or greater than, the effective length of the insertion section 2a of endoscope 2. As is shown in FIG. 4A, the tube 9 is fixed to the insertion section 2a of endoscope 2 by means of a medical tape 10, etc.

Moreover, as shown in FIG. 1A, a distal end portion of the tube 9 is provided with a distal-side coupling section 11, and a proximal end portion of the tube 9 is provided with a proximal-side coupling section 12. The distal-side coupling section 11 is detachably attached to the distal end portion 2b of the insertion section 2a of endoscope 2. The proximal-side coupling section 12 is coupled, as shown in FIG. 4A, to the proximal-side operation section 2c of endoscope 2.

As is shown in FIG. 2, the distal-side coupling section 11 includes a substantially cylindrical endoscope attachment section 13 and a substantially cylindrical cap section 14. The endoscope attachment section 13 is detachably fitted on the distal end portion 2b of insertion section 2a of endoscope 2. The cap section 14 is formed of a large-diameter cylindrical body disposed at the distal end of the endoscope attachment section 13. The cap section 14 constitutes a hood for the endoscope.

As is shown in FIG. 2, an endoscope engaging portion 15 is provided at the distal end portion of the endoscope attachment section 13 so as to project inward. When the resection instrument 1 is to be fixed to the endoscope 2, the distal end portion 2b of endoscope 2 is inserted in the endoscope attachment section 13. In this case, as shown in FIG. 2, the distal end portion 2b of endoscope 2 is pushed in until it abuts on the endoscope engaging portion 15. Thereby, the endoscope attachment section 13 is detachably fixed on the distal end portion 2b of endoscope 2 in the state in which the distal end portion 2b of endoscope 2 is prevented from entering the cap section 14.

A flange-like stepped portion is formed between the proximal end portion of the cap section 14 and the distal end portion of the endoscope attachment section 13. A communication port section 16 for communication with the inside of the cap section 14 is formed at the stepped portion. Further, the tube 9 is disposed on the outside of the endoscope attachment section 13. The distal end portion of the tube 9 is connected to the communication port section 16. The distal end portion of the tube 9 is air-tightly fixed to the endoscope attachment section 13 and cap section 14 by means of adhesion, welding, etc. The distal end of the tube 9 is open to the inside of the cap section 14. The axis of the tube 9 and the axis of the cap section 14 are substantially parallel at the connection portion between the tube 9 and cap section 14. The distal opening of the tube 9 is adjacent to the inner wall of the cap section 14.

An inclined face 17, which is inclined to the insertion direction of the endoscope 2, is formed at the distal end edge of the cap section 14. The communication port section 16 is disposed at a position where the degree of projection of the inclined face 17 is minimum (i.e. at a rearmost position). A flange-like small-diameter first projection portion 18, which projects inward, is provided along the inclined face 17 at the distal end of the cap section 14. The first projection portion 18 at the distal end edge of the cap section 14 may be formed along a plane perpendicular to the insertion direction of the endoscope 2.

Figure 3:
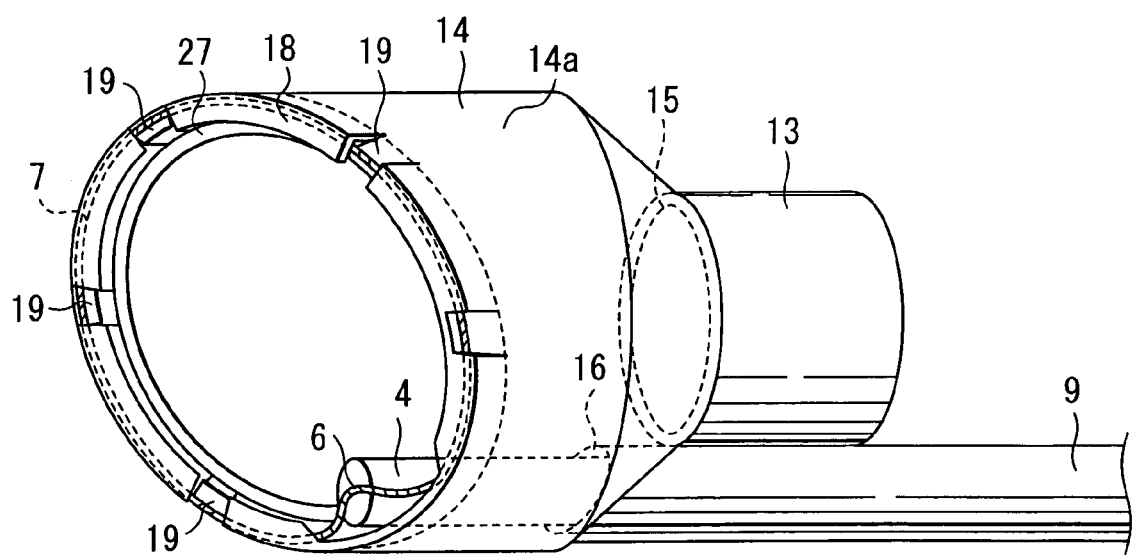
FIG. 3 is a perspective view showing the distal-side coupling section of the endoscopic mucous membrane resection instruction according to the first embodiment.

As is shown in FIG. 3, engaging portions 19 are formed at a plurality of locations along the periphery of a curved portion between a peripheral wall portion 14a of cap section 14 and the first projection portion 18. Each engaging portion 19 is formed by inwardly bending a peripheral portion of the curved portion.

In the case where the resection instrument 1 according to the present embodiment is used in combination with the diathermic snare 3, the flexible sheath 4 of diathermic snare 3 is inserted in the tube 9, as shown in FIG. 2, and the flexible sheath 4 is projected from the distal opening of the tube 9 into the cap section 14. In this state, the snare wire 6 is fed out of the sheath 4. At this time, as shown in FIGS. 2 and 3, the loop portion 7 of diathermic snare 3 is broadened and disposed along the inner periphery of the cap section 14. In this state, the loop portion 7 of snare wire 6 is held on outer surfaces of the engaging portions 19 so that the snare wire 6 is supported alternately by the engaging portions 19 and the first projection portion. Thereby, the loop portion 7 of diathermic snare 3 is held on the cap section 14.

As is shown in FIG. 1A, the proximal-side coupling section 12 of the tube 9 is provided with a hook member 20. The hook member 20, as shown in FIG. 4A, is detachably engaged with the proximal-side operation section 2c of endoscope 2. An engaging hole 21 is formed at one end portion of the hook member 20. The hook member 20 is engaged with a part of the proximal-side operation section 2c of endoscope 2. For example, the forceps cap 2e of the treatment instrument insertion section 2d is inserted and hooked in the engaging hole 21. In this way, the hook member 20 is detachably hooked around the forceps cap 2e of the endoscope 2.

The other end portion of the hook member 20 is provided with a treatment instrument insertion section 22. The treatment instrument insertion section 22 is provided with a cylindrical insertion guide member 22a. The guide member 22a is fixed to an end portion of the hook member 20. A through-hole 22b communicating with the tube 9 is formed in the cylindrical guide member 22a. The sheath 4 of diathermic snare 3 is inserted into the tube 9 from the treatment instrument insertion section 22 of hook member 20.

In addition, a treatment instrument fixing section 23 for detachably engaging the sheath 4 of diathermic snare 3 is provided on the guide member 22a. A male screw portion 22c is formed on the outer peripheral surface of the guide member 22a. Further, the treatment instrument fixing section 23 is provided with a rotation ring 24. A screw hole portion 24a is formed at a distal end portion of the rotation ring 24. The screw hole portion 24a is meshed with the male screw portion 22c of the guide member 22a.

A proximal end portion of the rotation ring 24 is provided with an elastic tube holder 24b. The elastic tube holder 24b includes an elastic tube 25. A distal end portion of the elastic tube 25 is held in the state in which it is abutted on the guide member 22a.

As is shown in FIG. 1B, a knob 24c is provided on the outer periphery of the rotation ring 24. The rotation ring 24 is rotated by handling the knob 24c, whereby the screw hole portion 24a of rotation ring 24, which is meshed with the male screw portion 22c of guide member 22a, is advanced relative to the male screw portion 22c. If the rotation ring 24 is rotated by the knob 24c in the direction of tightening, the elastic tube 25 within the elastic tube holder 24b is collapsed and elastically deformed so as to narrow the inner hole. Accordingly, the sheath 4 of the diathermic snare 3 inserted in the elastic tube 25 is detachably engaged by rotating the rotation ring 24 in the direction of tightening in the state in which the sheath 4 of diathermic snare 3 is inserted in the tube 9 from the treatment instrument insertion section 22 of hook member 20, as shown in FIG. 1A.

On the other hand, if the rotation ring 24 is loosened by rotating the rotation ring 24 by means of the knob 24c in a direction reverse to the direction of tightening (i.e. tightening-release direction), the collapsed and narrowed inner hole of the elastic tube 25 within the rotation ring 24 is restored to the original shape. By the operation of loosening the rotation ring 24, the engagement of the sheath 4 of the diathermic snare 3 is released and the sheath 4 is made advanceable.

A restriction member 26 for restricting axial movement of the slider 8b is detachably attached to the operation section 8 of diathermic snare 3. The restriction member 26 includes projection portions 26a and a fixing portion 26b. The projection portions 26a engage the finger hook portions 8c of the slider 8b. The fixing portion 26b fixes the restriction member 26 to the guide member 8a. By attaching the restriction member 26 to the operation section 8 of the diathermic snare 3, the snare wire 6 disposed in the cap section 14 is locked.

As is shown in FIGS. 2 and 3, the resection instrument 1 of the present embodiment has a flange-like small-diameter second projection portion 27, which is provided on the inner peripheral surface of the cap section 14. The second projection portion 27 is projected inward near the first projection portion 18 that is provided at the distal end edge of the cap section 14, such that the second projection portion 27 and first projection portion 18 are opposed to each other at a distance.

The operation of the resection instrument 1 with the above-described structure according to the present embodiment will now be described. Specifically, referring to FIGS. 4A through 12B, a description is given of the case where a living tissue in the body, for example, a mucous membrane A1 including a relatively large target part A0, is resected using the resection instrument 1 of this embodiment.

To begin with, the resection instrument 1 is mounted on the distal end portion 2b of the insertion section 2a of endoscope 2. At this time, as shown in FIG. 1A, the diathermic snare 3 is set in the resection instrument 1 in advance. In this state, the distal-side coupling section 11 of the resection instrument 1 is fitted on the distal end portion 2b of endoscope 2. Then, the tube 9 is disposed along the insertion section 2a of endoscope 2, and the tube 9 is fixed to the insertion section 2a by means of a medical tape 10, etc. Subsequently, as shown in FIG. 4A, the hook member 20 of the proximal-side coupling section 12 of resection instrument 1 is hooked around the forceps cap 2e of endoscope 2 and fixed.

In this state, the endoscope 2 and resection instrument 1 are inserted into the body cavity, and the distal opening portion of the cap section 14 of resection instrument 1 is moved toward a target to-be-resected mucous membrane part A2.

Then, the distal opening portion of the cap section 14 is pushed on the mucous membrane A1. In this state, a suction force is made to act within the cap section 14 from a suction device (not shown) via the channel of the endoscope 2. Thereby, the mucous membrane A1 is sucked in the cap section 14 by a negative pressure, and the to-be-resected part A2 of mucous membrane A1 is raised, as shown in FIG. 4B. At this time, when the target part A0 is large, only a part of the target part A0 is sucked in the cap section 14 and the entire target part A0 is not sucked.

Thereafter, as shown in FIG. 5A, the restriction member 26 is removed from the operation section 8 of the diathermic snare 3. In this state, the slider 8b of operation section 8 is retreated relative to the guide member 8a. By this operation, the snare wire 6 is disengaged from the engaging portions 19 and pulled into the sheath 4. Thereby, as shown in FIG. 5B, the loop portion 7 of the snare wire 6 is reduced to tightly bind a proximal portion of the to-be-resected part A2 of mucous membrane A1.

Following the above, as shown in FIG. 6A, the knob 24c of the treatment instrument fixing section 23 is held and rotated, and thus the rotation ring 24 is rotated to loosen the tightening of the elastic tube 25. Thereby, the engagement of the sheath 4 of the diathermic snare 3 is released. In this state, the sheath 4 is pushed forward.

By the pushing operation of the sheath 4, as shown in FIG. 6B, the distal end portion of the sheath 4 is projected from the cap section 14, and the to-be-resected part A2 that is tightly bound by the loop portion 7 of snare wire 6 is put out of the cap section 14. Subsequently, the state of the mucous membrane A1 and muscular layer A3 is examined using, e.g. an ultrasonic probe passed through the channel of the endoscope 2, and it is confirmed whether the muscular layer A3 is included in the to-be-resected part A2. This ensures safe resection of the mucous membrane A1.

In the state shown in FIG. 6B, while the to-be-resected part A2 is strangulated by the loop portion 7 of snare wire 6, a high-frequency current is let to flow to the snare wire 6, thereby performing a first resection work for resecting the target part A0 of mucous membrane A1. At this time, as shown in FIG. 7B, only a portion of the target part A0 is resected.

Following the completion of the first resection work for resecting the target part A0 of mucous membrane A1, the diathermic snare 3 used in the first resection work is removed from the resection instrument 1 (see FIG. 7A).

Next, a second resection work for resecting the other portion of the target part A0, which is not resected by the first resection work, is performed. In the second resection work, in the state in which the diathermic snare 3 is not set in the resection instrument 1, the distal opening portion of the cap section 14 of resection instrument 1 is moved toward a target to-be-resected mucous membrane part, that is, toward the mucous membrane A1 of the remaining target part A0, like the first resection work.

Figure 8A:
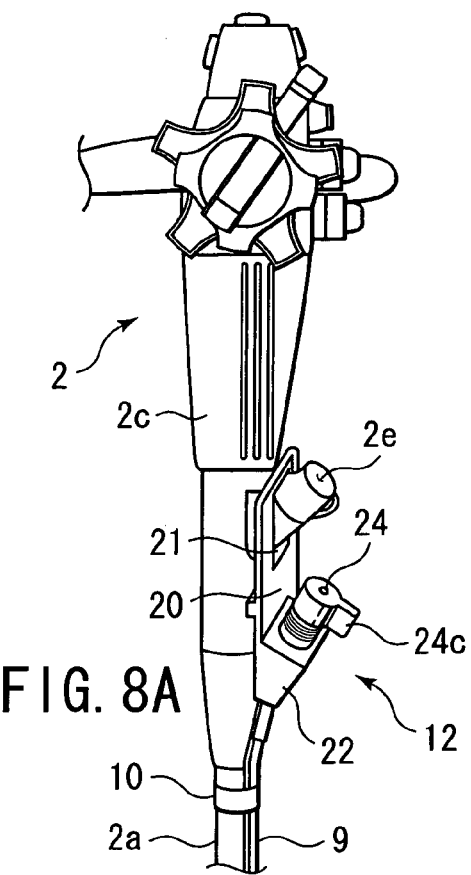
FIG. 8A is a perspective view showing a state prior to insertion of a second diathermic snare into the endoscopic mucous membrane resection instrument according to the first embodiment.
Figure 8B:
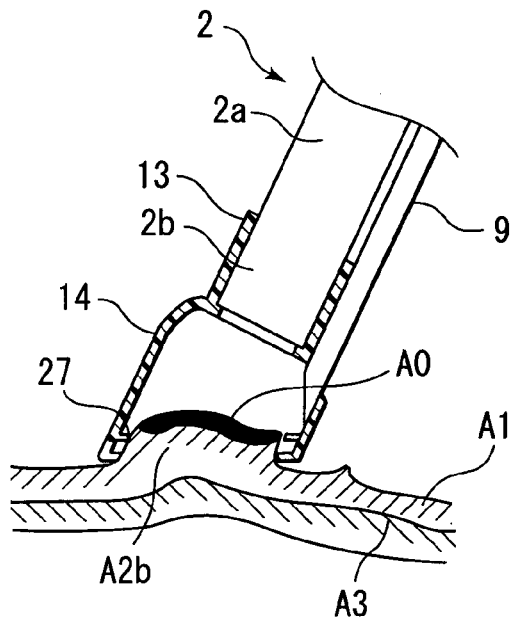
FIG. 8B is a vertical cross-sectional view of the main part, showing the state in which a second to-be-resected portion of the mucous membrane is sucked in the cap section and relatively slightly raised.

The distal opening portion of the cap section 14 is pushed on the mucous membrane A1 of the target part A0, as shown in FIG. 8B. In this state, the mucous membrane A1 is weakly sucked from the suction device (not shown) via the channel of the endoscope 2. Thereby, the mucous membrane A1 is sucked in the cap section 14, and a second to-be-resected part A2b of the mucous membrane A1 is relatively slightly raised.

Figure 9A:
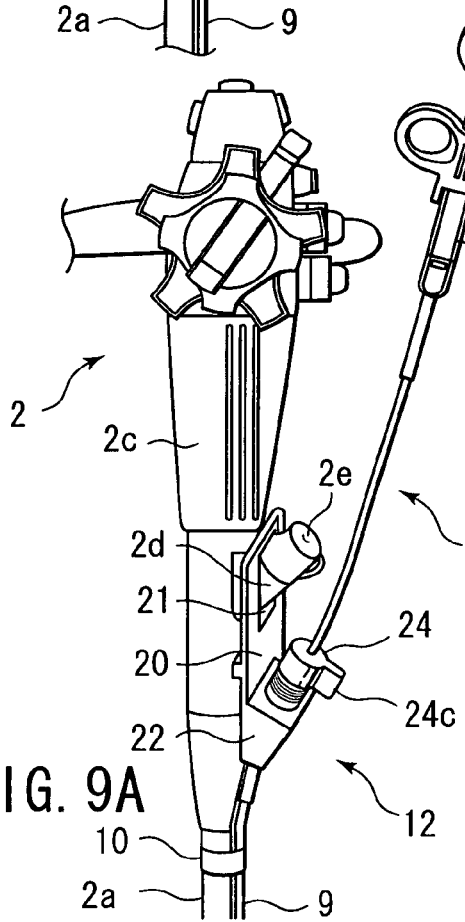
FIG. 9A is a perspective view showing the state in which a second diathermic snare is inserted in the endoscopic mucous membrane resection instrument according to the first embodiment.
Figure 9B:
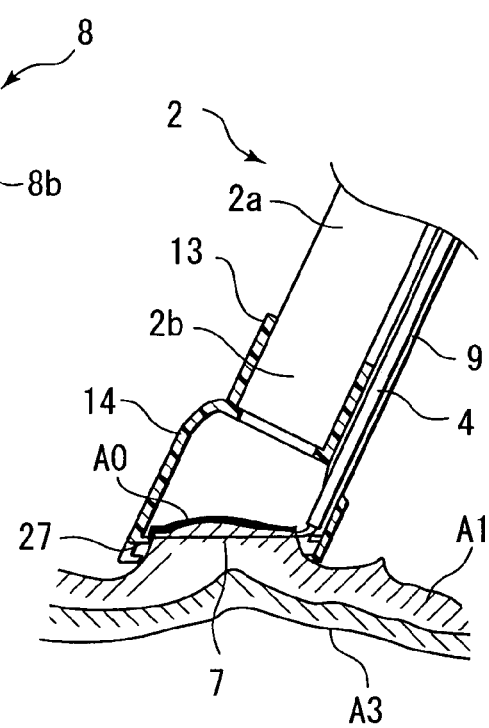
FIG. 9B is a vertical cross-sectional view of the main part, showing the state in which a loop portion of the second diathermic snare is circumferentially broadened along the inner periphery of the cap section and disposed on a second projection portion.

Then, in this state, as shown in FIG. 9A, a second diathermic snare 31 is inserted into the tube 9 from the treatment instrument insertion section 22 of hook member 20. In the state in which the sheath 4 of the diathermic snare 31 is projected into the inside of the cap section 14 from the distal opening portion of the tube 9, the snare wire 6 is fed out of the sheath 4. At this time, as shown in FIG. 9B, the loop portion 7 of the second diathermic snare 31 is broadened along the inner periphery of the cap section 14 and disposed on the second projection portion 27.

Figure 10A:
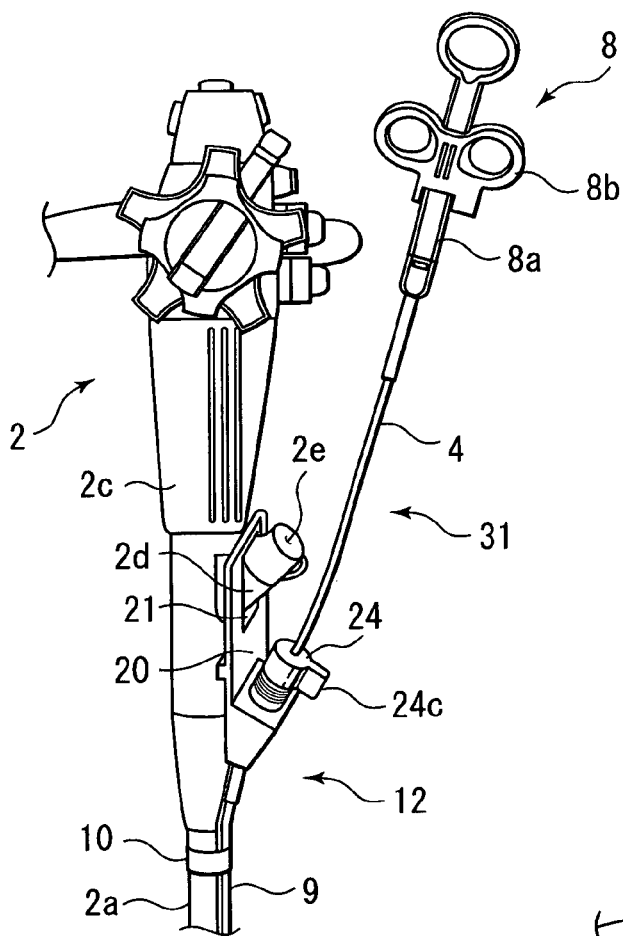
FIG. 10A is a perspective view showing the state in which the second diathermic snare is inserted in the endoscopic mucous membrane resection instrument according to the first embodiment.
Figure 10B:
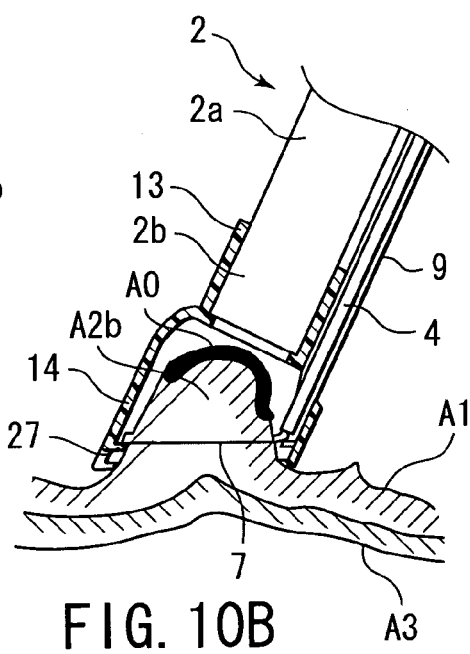
FIG. 10B is a vertical cross-sectional view of the main part, showing the state in which the second to-be-resected portion of the mucous membrane is largely raised.

In this state, the second to-be-resected part A2b of the mucous membrane A1 is sucked more strongly than before the insertion of the second diathermic snare 31, and is largely raised, as shown in FIG. 10B.

Figure 11B:
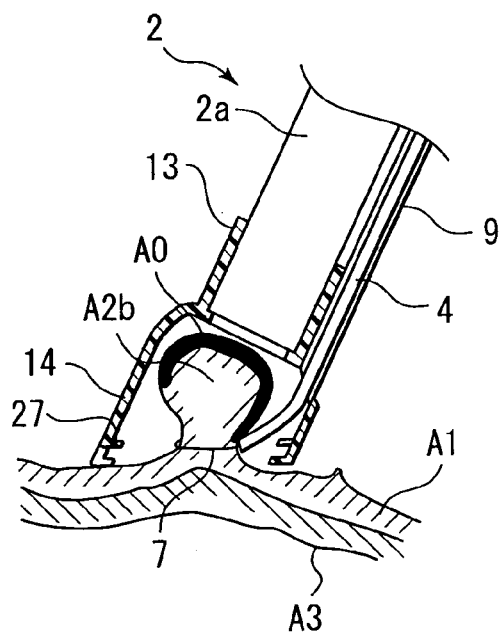
FIG. 11B is a vertical cross-sectional view of the main part, showing the state in which a loop portion of a snare wire is reduced to tightly bind a proximal portion of the to-be-resected portion of the mucous membrane.
Figure 11A:
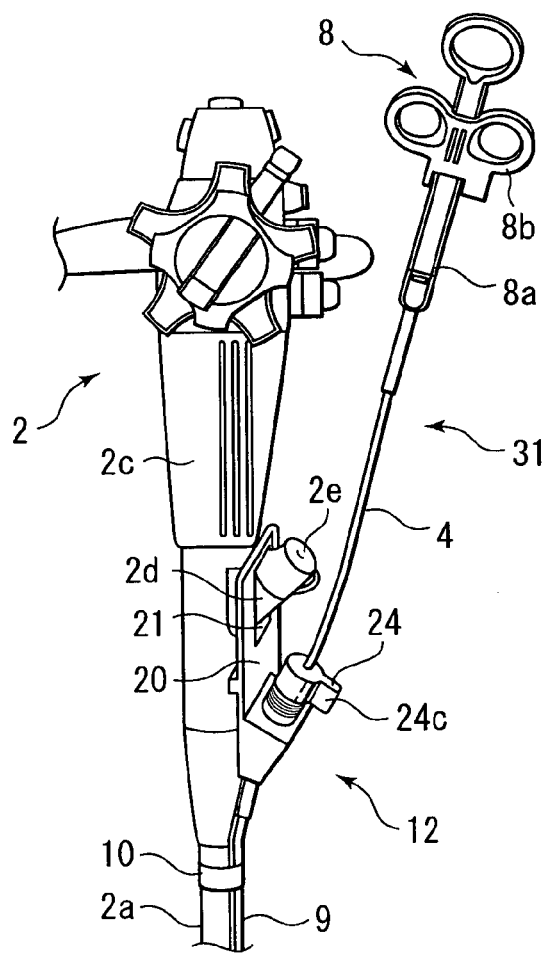
FIG. 11A is a perspective view showing the state in which a slider of an operation section of the second diathermic snare of the endoscopic mucous membrane resection instrument according to the first embodiment is retreated relative to a guide member.
Figure 12A:
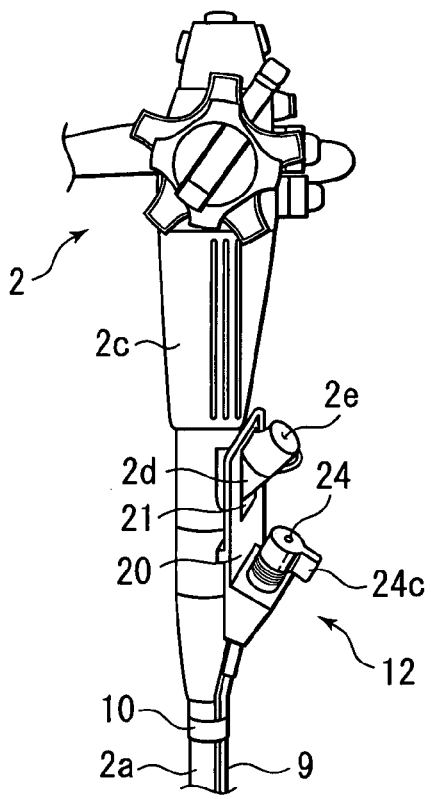
FIG. 12A is a perspective view showing the state in which the second diathermic snare is removed from the endoscopic mucous membrane resection instrument according to the first embodiment.
Figure 12B:
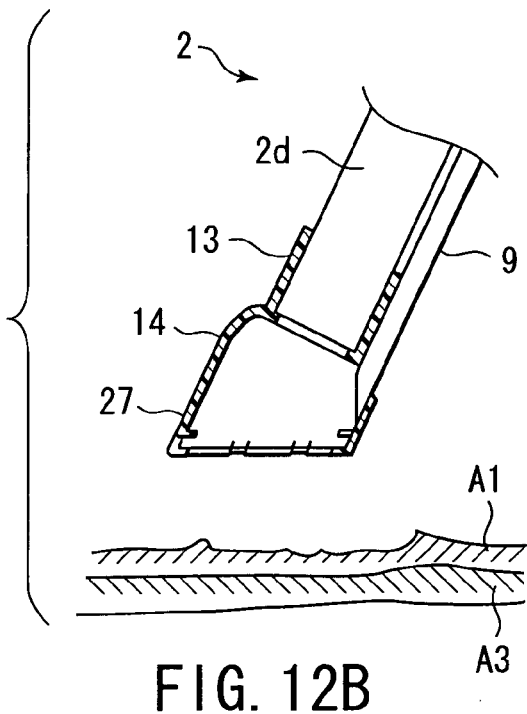
FIG. 12B is a vertical cross-sectional view of the main part, showing the completion state of the second resection work.

Thereafter, as shown in FIG. 11A, the slider 8b of operation section 8 of second diathermic snare 31 is retreated relative to the guide member 8a. By this operation, the snare wire 6 is disengaged from the second projection portion 27 and pulled into the sheath 4. Thereby, as shown in FIG. 11B, the loop portion 7 of snare wire 6 is reduced to tightly bind a proximal portion of the second to-be-resected part A2b of the mucous membrane A1.

Then, like the first resection work, the sheath 4 is pushed forward and the to-be-resected part A2b that is tightly bound by the snare wire 6 is put out of the cap section 14 (see FIG. 6B). In this state, using, e.g. an ultrasonic probe passed through the channel of the endoscope 2, the state of the mucous membrane A1 and muscular layer A3 is examined and it is confirmed whether the muscular layer A3 is included in the to-be-resected part A2b. Subsequently, while the to-be-resected part A2b is strangulated by the loop portion 7 of snare wire 6, a high-frequency current is let to flow to the snare wire 6, thereby performing a second resection work for resecting the remaining target part A0 (to-be-resected part A2b).

Following the completion of the second resection work, the ultrasonic probe, etc. are removed from the channel. In this state, the part A2b of the mucous membrane A1 is sucked in the cap section 14 by a sucking force applied from the suction device (not shown) via the channel of the endoscope 2. At this time, the resected part A2 of mucous membrane A1, which has been resected by the first resection work, is also sucked in the cap section 14 along with the second resected part A2b of mucous membrane A1. Thus, the second resected part A2b of mucous membrane A1 and the resected part A2 of the mucous membrane A1 resected by the first resection work are sucked and held in the cap section 14 and are recovered to the outside of the body cavity along with the endoscope 2.

The embodiment with the above structure has the following advantages. The resection instrument 1 of this embodiment is provided with the flange-like small-diameter second projection portion 27 near the first projection portion 18 formed at the distal end edge of the cap section 14. Thus, after the snare wire 6 of diathermic snare 3 is set on the first projection portion 18 and used in the first resection work, the snare wire 6 of diathermic snare 31 to be used in the second resection work can be set on the second projection portion 27 that is different from the first projection portion 18. Accordingly, when the mucous membrane A1 including the relatively large target part A0 is divided into a plurality of portions and resected, it is possible to smoothly perform the second looping work for setting the loop portion 7 of snare wire 6 of diathermic snare 31 on the second projection portion 27. Therefore, it is advantageously possible to easily perform a treatment in which a large target part is divided into a plurality of portions and endoscopic mucous membrane resection is performed twice or more for resecting the divided portions.

Figure 13:
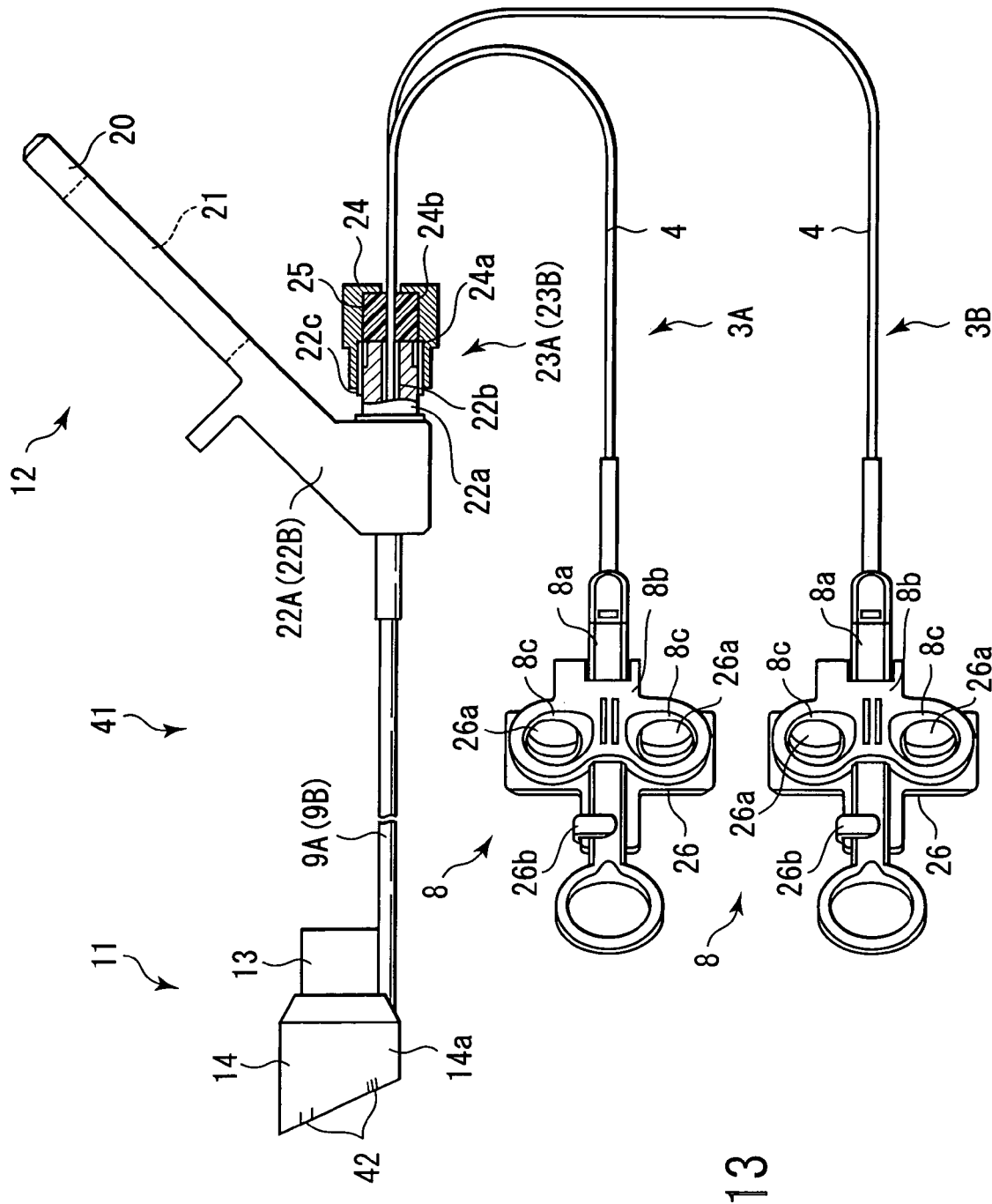
FIG. 13 is a side view showing an endoscopic mucous membrane resection instrument according to a second embodiment of the present invention.

FIGS. 13 through 23B show a second embodiment of the present invention. FIG. 13 schematically shows the whole structure of an endoscopic mucous membrane resection instrument 41 according to the second embodiment. In the endoscopic mucous membrane resection instrument 41 according to the second embodiment, the resection instrument 1 of the first embodiment (see FIGS. 1A through 12B) is partly altered, as described below, and two diathermic snares 3A and 3B can be attached at the same time. In the other respects, the structure of the endoscopic mucous membrane resection instrument 41 is the same as that of the resection instrument 1 of the first embodiment. The parts common to those of the resection instrument 1 are denoted by like reference numerals, and a description thereof is omitted.

The endoscopic mucous membrane resection instrument 41 according to the second embodiment is provided with two tubes 9A and 9B. As is shown in FIG. 15A, two communication port sections 16A and 16B, which communicate with the inside of the cap section 14, are formed at a flange-like stepped portion between the proximal end portion of the cap section 14 of distal-side coupling section 11 and the distal end portion of the endoscope attachment section 13. The two communication port sections 16A and 16B are laterally disposed along the periphery of the cap section 14 at a position where the degree of projection of the inclined face 17 formed at the distal end edge of the cap section 14 is minimum (i.e. at a rearmost position). Further, as shown in FIG. 16A, two tubes 9A and 9B are juxtaposed on the outside of the endoscope attachment section 13.

Distal end portions of the tubes 9A and 9B are connected to the communication port sections 16A and 16B.

The first diathermic snare 3A is inserted in the tube 9A, and the second diathermic snare 3B is inserted in the other tube 9B. Each of the diathermic snares 3A and 3B has the same structure as the diathermic snare 3 of the first embodiment. The components common to the diathermic snare 3 of the first embodiment are denoted by like reference numerals, and a description thereof is omitted.

Distal end portions of the diathermic snares 3A and 3B are projected into the cap section 14 from the communication port sections 16A and 16B. Snare wires 6 of the diathermic snares 3A and 3B are fed out of the sheaths 4 and held on the cap section 14 in the manner described below.

As is shown in FIG. 15A, a plurality of inwardly bent engaging portions 42 are provided at a plurality of locations along the periphery of a curved portion between the projection portion 18 formed at the distal end of the cap section 14 and the peripheral wall portion 14a of the cap section 14. Each engaging portions 42, as shown in FIG. 15B, is formed such that a lateral notch 42a is formed at a substantially central portion of the projection portion 18 and two longitudinal notches 42b are formed from both ends of the notch 42a to the peripheral wall portion 14a of the cap section 14, and the portion defined by the notches is bent inward.

Figure 14A:
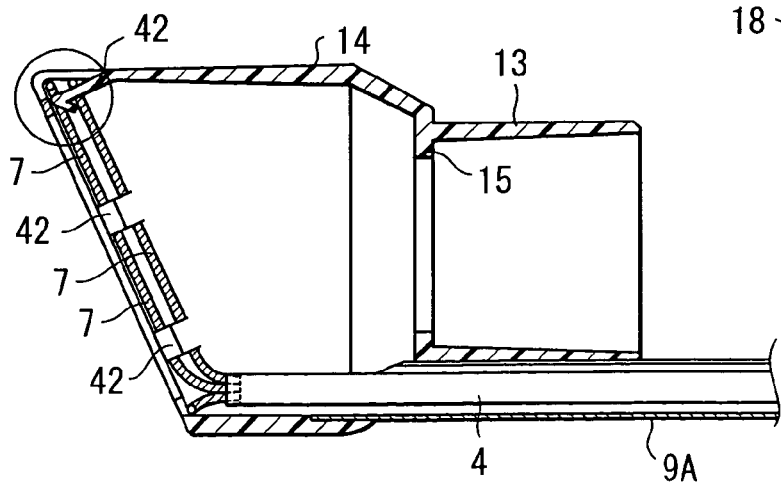
FIG. 14A is a vertical cross-sectional view of a main part, showing the state in which two diathermic snares are set in the cap section of the endoscopic mucous membrane resection instrument according to the second embodiment.
Figure 14B:
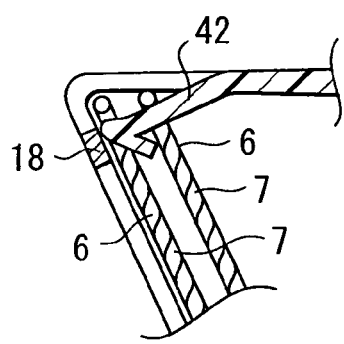
FIG. 14B is a vertical cross-sectional view of the main part, showing the state in which an encircled part in FIG. 14A is enlarged.

When the two diathermic snares 3A and 3B are set in the endoscopic mucous membrane resection instrument 41 of this embodiment, the snare wires 6 are fed out of the sheaths 4 in the state in which the sheaths 4 of the diathermic snares 3A and 3B are projected into the cap section 14 from the distal opening portions of the tubes 9A and 9B. At this time, as shown in FIG. 14A, the loop portions 7 of diathermic snares 3A and 3B are disposed along the peripheral surface of the cap section 14. Thus, the two loop portions 7 are arranged forward and backward on the inner peripheral surface of the cap section 14. In this case, the snare wire 6 of the first diathermic snare 3A is disposed on the distal end side, and the snare wire 6 of the second diathermic snare 3B is disposed on the proximal end side. In this state, the loop portions 7 of the two snare wires 6 are held on the outer surfaces of the engaging portions 42, whereby the snare wire 6 of the first diathermic snare 3A is supported alternately between the engaging portions 42 and the projection portion 18 and the snare wire 6 of the second diathermic snare 3B is supported alternately between the engaging portions 42 and the inner wall portion 14a of the cap section 14. Thereby, the loop portions 7 of the diathermic snares 3A and 3B are held on the cap section 14 at the same time.

As is shown in FIG. 13, a restriction member 26 for restricting axial movement of the slider 8b is detachably attached to the operation section 8 of each of the diathermic snares 3A and 3B. By attaching the restriction member 26 to the operation section 8 of each diathermic snare 3A, 3B, the snare wire 6 disposed in the cap section 14 is locked.

As is shown in FIG. 16B, two treatment instrument insertion sections 22A and 22B are laterally disposed at the end portion of the hook member 20 of the distal-side coupling section 12. The respective treatment instrument insertion sections 22A and 22B are provided with treatment instrument fixing sections 23A and 23B for detachably engaging the sheaths 4 of the diathermic snares 3A and 3B. Each of the treatment instrument fixing sections 23A and 23B has the same structure as the treatment instrument fixing section 23 according to the first embodiment.

The operation of the endoscopic mucous membrane resection instrument 41 with the above-described structure according to the present embodiment will now be described.

Specifically, referring to FIGS. 17A through 23B, a description is given of the case where a living tissue in the body, for example, a mucous membrane A1 including a relatively large target part A0, is resected using the endoscopic mucous membrane resection instrument 41 of this embodiment.

Figure 17A:
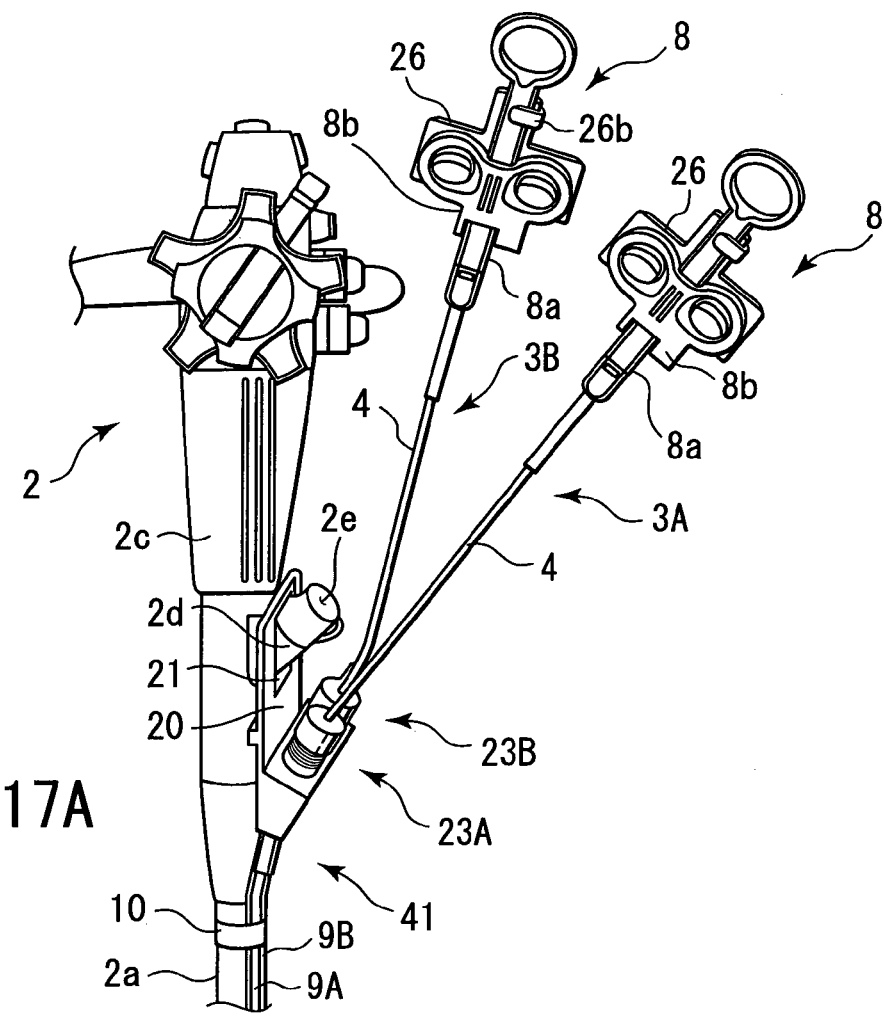
FIG. 17A is a perspective view showing a fixed state of the proximal-side coupling section of the endoscopic mucous membrane resection instrument according to the second embodiment.

Like the first embodiment, the endoscopic mucous membrane resection instrument 41 is mounted on the distal end portion 2b of the insertion section 2a of endoscope 2. At this time, as shown in FIG. 17A, the two diathermic snares 3A and 3B are set in the endoscopic mucous membrane resection instrument 41 in advance. In this state, the endoscopic mucous membrane resection instrument 41 is inserted into the body cavity, and the distal opening portion of the cap section 14 is moved toward a target to-be-resected mucous membrane part A2.

Figure 17B:
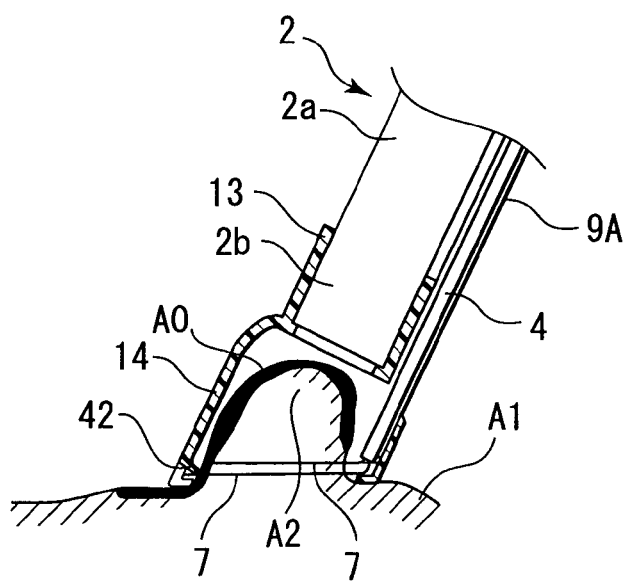
FIG. 17B is a vertical cross-sectional view of the main part, showing the state in which a target to-be-resected mucous membrane part is raised.

Then, the distal opening portion of the cap section 14 is pushed on the mucous membrane A1. In this state, a suction force is made to act within the cap section 14 via the channel of the endoscope 2. Thereby, the mucous membrane A1 is sucked in the cap section 14, and the to-be-resected part A2 of mucous membrane A1 is raised, as shown in FIG. 17B. At this time, when the target part A0 is large, only a part of the target part A0 is sucked in the cap section 14 and the entire target part A0 is not sucked.

Figure 18A:
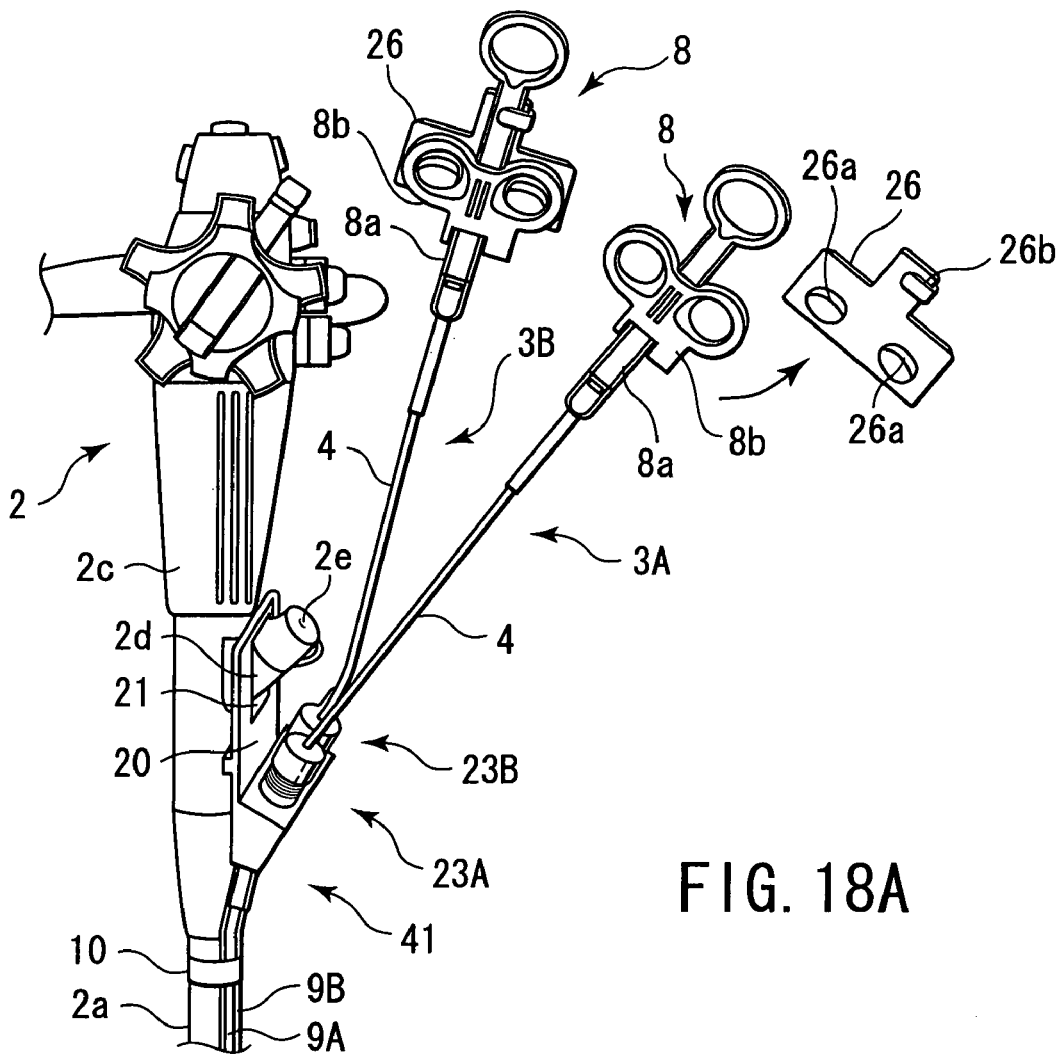
FIG. 18A is a perspective view showing the state in which a restriction member is removed from an operation section of a first diathermic snare of the endoscopic mucous membrane resection instrument according to the second embodiment.
Figure 18B:
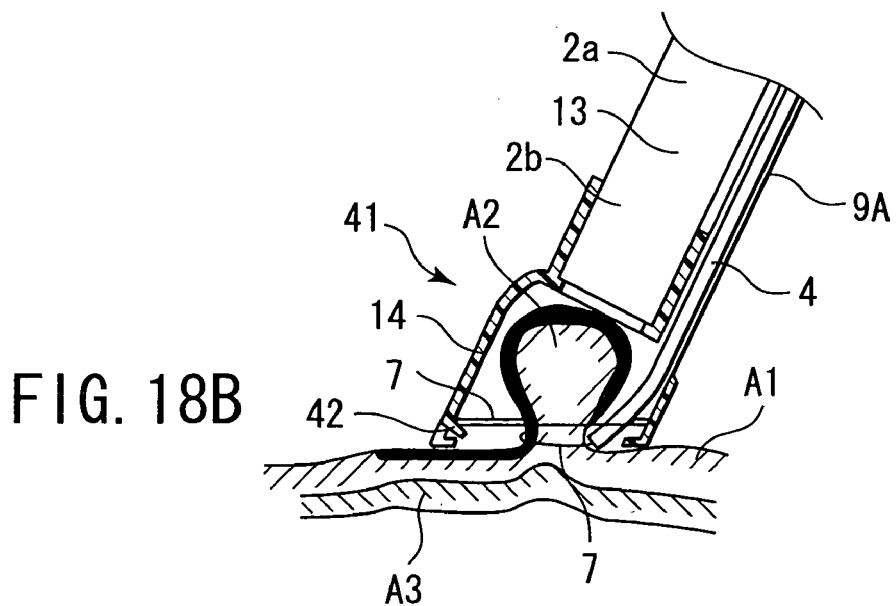
FIG. 18B is a vertical cross-sectional view of the main part, showing the state in which a loop portion of a snare wire is reduced to tightly bind a proximal portion of the target mucous membrane part.

Thereafter, as shown in FIG. 18A, the restriction member 26 is removed from the operation section 8 of the first diathermic snare 3A. In this state, the slider 8b of operation section 8 of first diathermic snare 3A is retreated relative to the guide member 8a. By this operation, the snare wire 6 is disengaged from the engaging portions 42 and pulled into the sheath 4. Thereby, as shown in FIG. 18B, the loop portion 7 of the snare wire 6 of first diathermic snare 3A is reduced to tightly bind a proximal portion of the to-be-resected part A2 of mucous membrane A1.

Figure 19A:
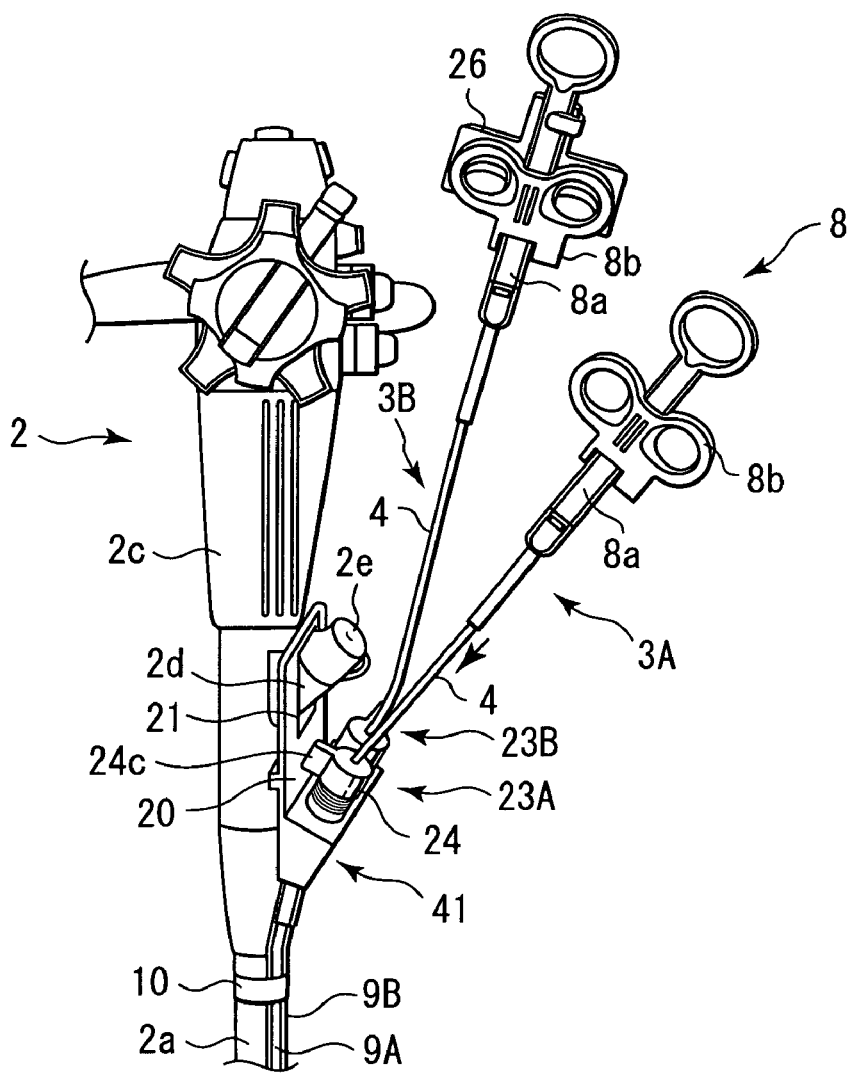
FIG. 19A is a perspective view showing the state in which the engagement of a sheath of the first diathermic snare of the endoscopic mucous membrane resection instrument according to the second embodiment is released.

Following the above, as shown in FIG. 19A, the knob 24c of the treatment instrument fixing section 23A is held and the rotation ring 24 is rotated to loosen the tightening of the elastic tube 25. Thereby, the engagement of the sheath 4 of the first diathermic snare 3 is released. In this state, the sheath 4 is pushed forward.

Figure 19B:
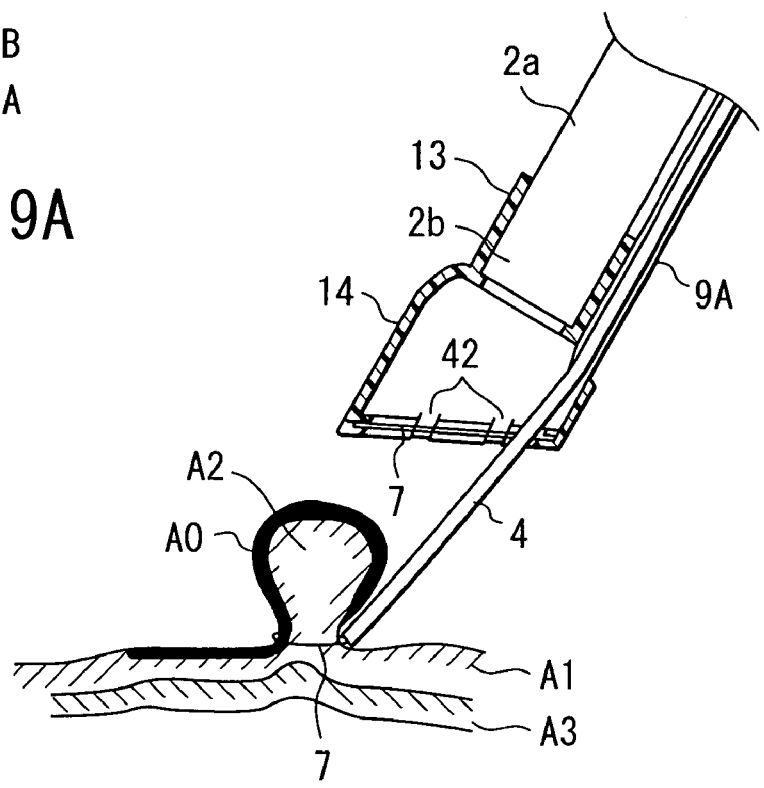
FIG. 19B is a vertical cross-sectional view of the main part, showing the state in which the distal end portion of the sheath is projected from the cap section.

By the pushing operation of the sheath 4, as shown in FIG. 19B, the distal end portion of the sheath 4 is projected from the cap section 14, and the to-be-resected part A2 that is tightly bound by the loop portion 7 of snare wire 6 is put out of the cap section 14. Subsequently, the state of the mucous membrane A1 and muscular layer A3 is examined using, e.g. an ultrasonic probe passed through the channel of the endoscope 2, and it is confirmed whether the muscular layer A3 is included in the to-be-resected part A2. This ensures safe resection of the mucous membrane A1.

In the state shown in FIG. 19B, while the to-be-resected part A2 is strangulated by the loop portion 7 of snare wire 6, a high-frequency current is let to flow to the snare wire 6, thereby performing a first resection work for resecting the target part A0 of mucous membrane A1. At this time, as shown in FIG. 20B, only a portion of the target part A0 is resected.

Following the completion of the first resection work for resecting the target part A0 of mucous membrane A1, the first diathermic snare 3A used in the first resection work is removed from the endoscopic mucous membrane resection instrument 41 (see FIG. 20A).

Next, a second resection work for resecting the other portion of the target part A0, which is not resected by the first resection work, is performed. In the second resection work, the distal opening portion of the cap section 14 of endoscopic mucous membrane resection instrument 41 is moved toward a target to-be-resected mucous membrane part for the second resection work, that is, toward the mucous membrane A1 of the remaining target part A0, like the first resection work, as shown in FIG. 20B.

The distal opening portion of the cap section 14 is pushed on the mucous membrane A1, as shown in FIG. 20C. In this state, the second to-be-resected part A2*b* of the mucous membrane A1 is sucked in the cap section 14.

Figures 21A, 21B:
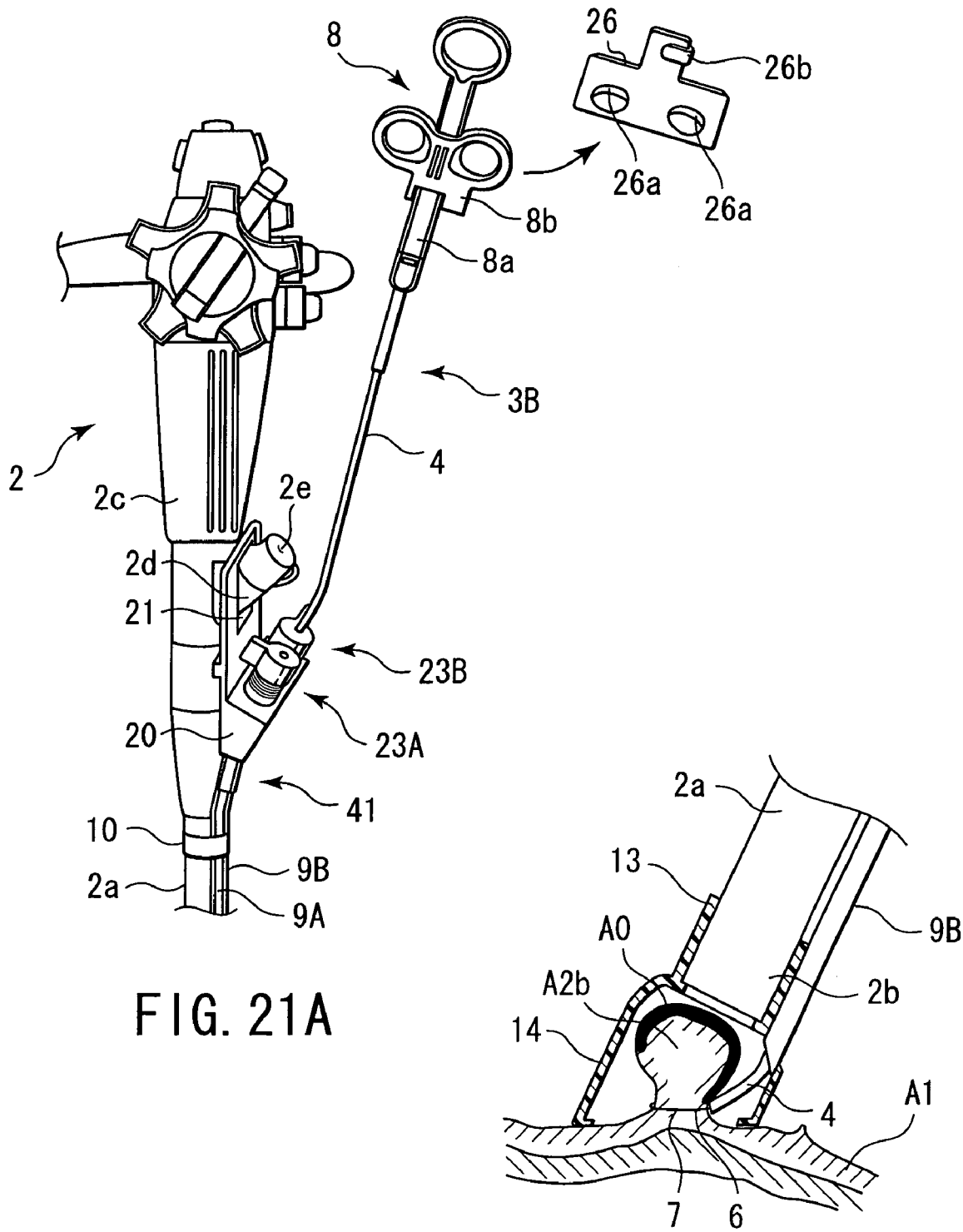
FIG. 21A is a perspective view showing the state in which a restriction member is removed from an operation section of the second diathermic snare of the endoscopic mucous membrane resection instrument according to the second embodiment.
FIG. 21B is a vertical cross-sectional view of the main part, showing the state in which a proximal portion of the second to-be-resected portion sucked in the cap section is tightly bound.

Then, in this state, as shown in FIG. 21A, the restriction member 26 is removed from the operation section 8 of the second diathermic snare 3B. In addition, the slider 8*b* of operation section 8 is retreated relative to the guide member 8*a*. By this operation, the snare wire 6 is disengaged from the engaging portions 42 and pulled into the sheath 4. Thereby, as shown in FIG. 21B, a proximal portion of the second to-be-resected part A2*b* of the mucous membrane A1 is tightly bound.

Figures 22A, 22B:
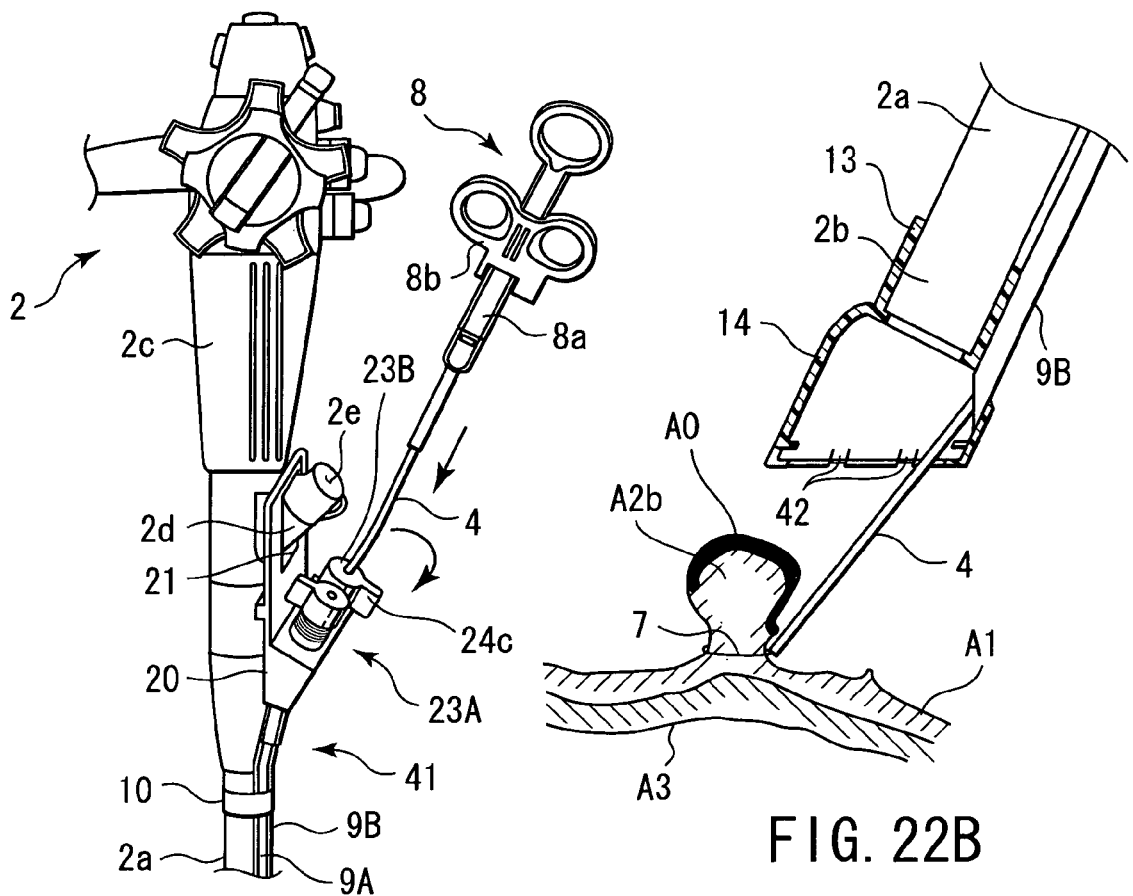
FIG. 22A is a perspective view showing the state in which the engagement of a sheath of the second diathermic snare of the endoscopic mucous membrane resection instrument according to the second embodiment is released.
FIG. 22B is a vertical cross-sectional view of the main part, showing the state in which the distal end portion of the sheath is projected from the cap section.
Figures 23A, 23B:
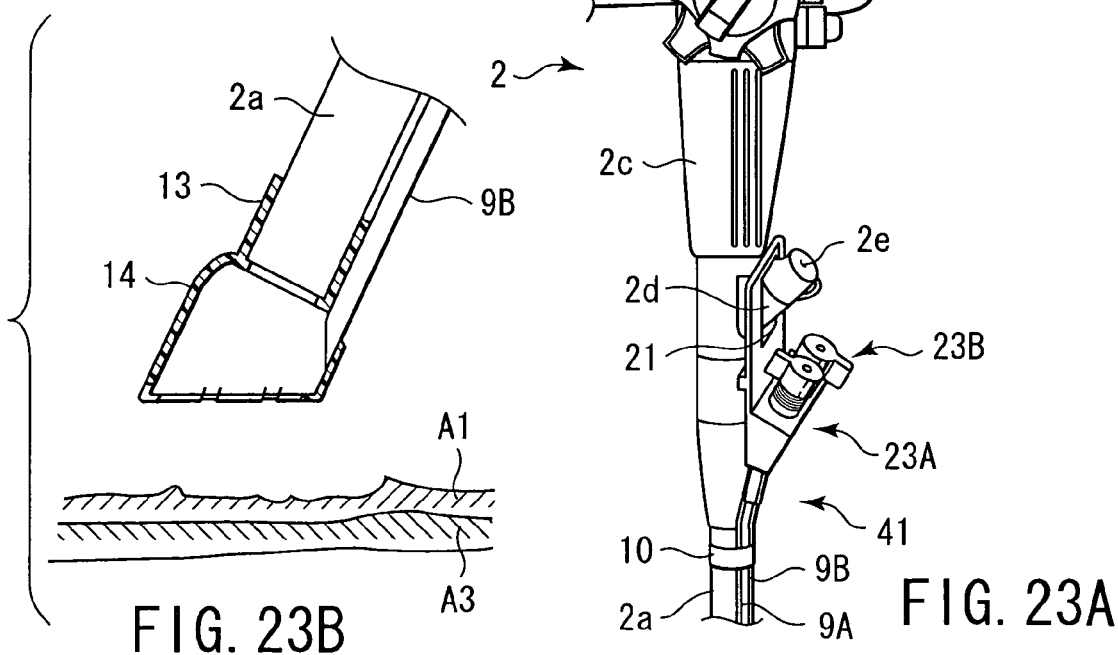
FIG. 23A is a perspective view showing the state in which the second diathermic snare is removed from the endoscopic mucous membrane resection instrument according to the second embodiment.
FIG. 23B is a vertical cross-sectional view of the main part, showing the completion state of the second resection operation of the mucous membrane.

Following the above, as shown in FIG. 22A, the knob 24*c* of the treatment instrument fixing section 23B is held and the rotation ring 24 is rotated to loosen the tightening of the elastic tube 25. Thereby, the engagement of the sheath 4 of the second diathermic snare 3B is released. In this state, the sheath 4 is pushed forward.

By the pushing operation of the sheath 4, as shown in FIG. 22B, the distal end portion of the sheath 4 is projected from the cap section 14, and the second to-be-resected part A2*b* that is tightly bound by the loop portion 7 of snare wire 6 is put out of the cap section 14. Subsequently, the state of the mucous membrane A1 and muscular layer A3 is examined using, e.g. an ultrasonic probe passed through the channel of the endoscope 2, and it is confirmed whether the muscular layer A3 is included in the second to-be-resected part A2*b*. This ensures safe resection of the mucous membrane A1.

Subsequently, in the state shown in FIG. 22B, while the second to-be-resected part A2*b* is strangulated by the loop portion 7 of snare wire 6, a high-frequency current is let to flow to the snare wire 6, thereby performing a second resection work for resecting the remaining target part A0 (to-be-resected part A2*b*).

Following the completion of the second resection work, the ultrasonic probe, etc. are removed from the channel. In this state, the part A2*b* of the mucous membrane A1 is sucked in the cap section 14 by a sucking force applied from the suction device (not shown) via the channel of the endoscope 2. At this time, the resected part A2 of mucous membrane A1, which has been resected by the first resection work, is sucked in the cap section 14 along with the second resected part A2*b* of mucous membrane A1. Thus, the second resected part A2*b* of mucous membrane A1 and the resected part A2 of the mucous membrane A1 resected by the first resection work are sucked and held in the cap section 14 and are recovered to the outside of the body cavity along with the endoscope 2.

The second embodiment with the above-described structure has the following advantages. In the endoscopic mucous membrane resection instrument 41 according to the second embodiment, the two tubes 9A and 9B are provided and the two diathermic snares 3A and 3B can be attached to the endoscopic mucous membrane resection instrument 41 at the same time. In addition, the snare wire 6 of the second diathermic snare 3B is disposed in advance on the inner peripheral surface of the cap section 14 near the proximal end side of the snare wire 6 of the first diathermic snare 3A disposed in advance at the projection portion 18 formed at the distal end of the cap section 14. Thus, after the completion of the first resection work using the snare wire 6 of the first diathermic snare 3A, the second resection work can be conducted using the snare wire 6 of the second diathermic snare 3B disposed in advance on the inner peripheral surface of the cap section 14 near the proximal end side of the snare wire 6 of the first diathermic snare 3A. Therefore, in the case where the mucous membrane A1 including the relatively large target part A0 is divided and resected by a plurality of resection operations, it is possible to omit, after the completion of the first resection work, the second looping work for setting the loop portion 7 of the snare wire 6 of the second diathermic snare 3B on the inner peripheral surface of the cap section 14. It is thus possible to easily perform the second resection work when endoscopic mucous membrane resection is conducted by dividing the target part.

Figure 24:
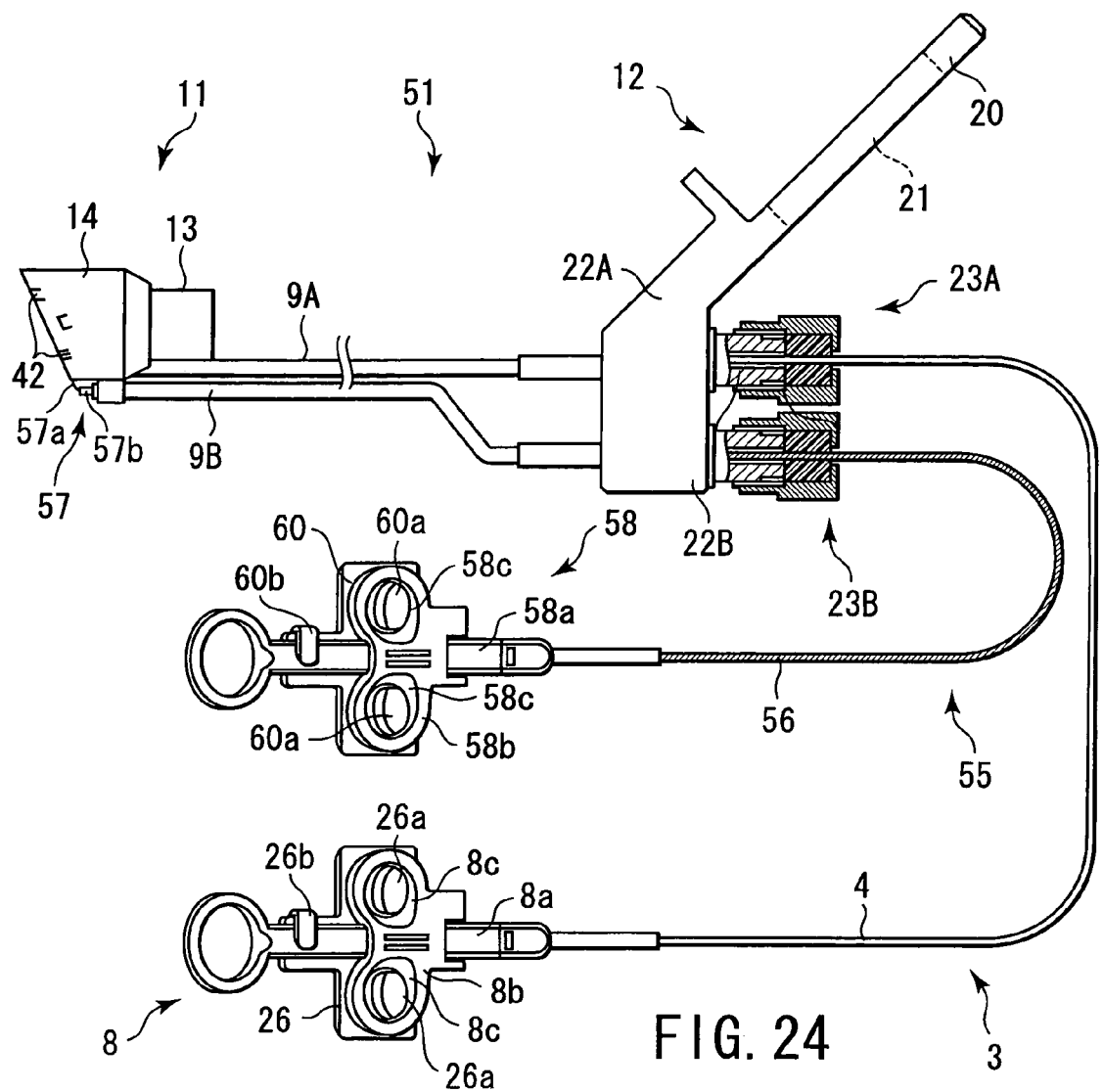
FIG. 24 is a side view showing an endoscopic mucous membrane resection instrument according to a third embodiment of the present invention.

FIGS. 24 through 35B show a third embodiment of the present invention. FIG. 24 schematically shows the whole structure of an endoscopic mucous membrane resection instrument 51 according to the third embodiment. In the endoscopic mucous membrane resection instrument 51 according to the third embodiment, the resection instrument 1 of the first embodiment (see FIGS. 1A through 12B) is partly altered, as described below. In the other respects, the structure of the endoscopic mucous membrane resection instrument 51 is the same as that of the resection instrument 1 of the first embodiment. The parts common to those of the resection instrument 1 are denoted by like reference numerals, and a description thereof is omitted.

The endoscopic mucous membrane resection instrument 51, like the endoscopic mucous membrane resection instrument 41 of the second embodiment (see FIGS. 13 through 23B), is provided with two tubes 9A and 9B.

Figure 25:
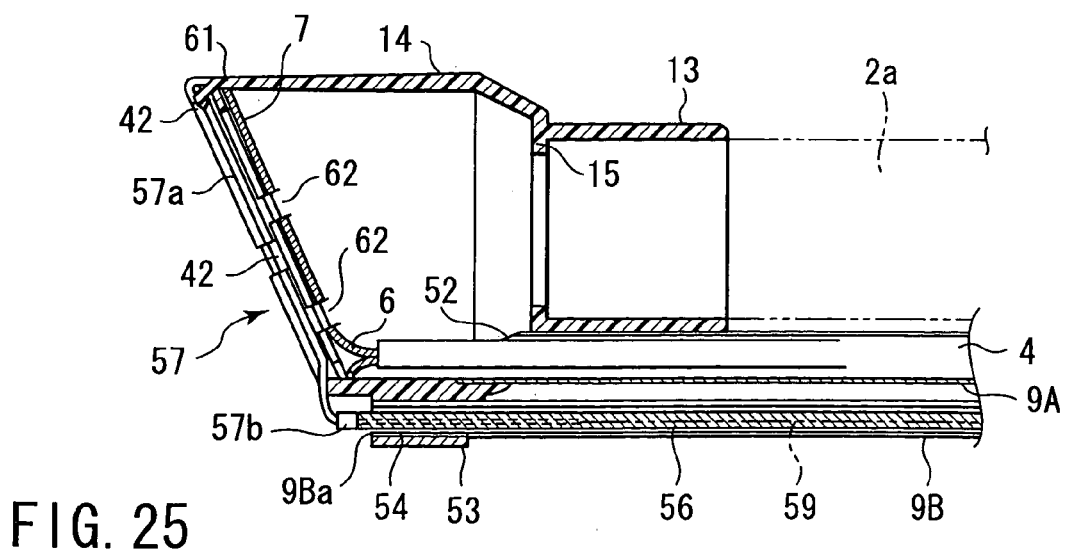
FIG. 25 is a vertical cross-sectional view of a main part, showing the state in which a ligation loop of a ligator and a snare wire of a diathermic snare are set in the cap section of the endoscopic mucous membrane resection instrument according to the third embodiment of the present invention.

In addition, as shown in FIG. 25, a communication port section 52 for communication with the inside of the cap section 14 is formed at the flange-like stepped portion formed between the proximal end portion of the cap section 14 and the distal end portion of the endoscope attachment section 13. The communication port section 52 is disposed at a position where the degree of projection of the inclined face 17 at the distal end edge of the cap section 14 is minimum (i.e. at a rearmost position). The first tube 9A is disposed on the outside of the endoscope attachment section 13. A distal end portion of the first tube 9A is connected to the communication port section 52.

Figure 26:
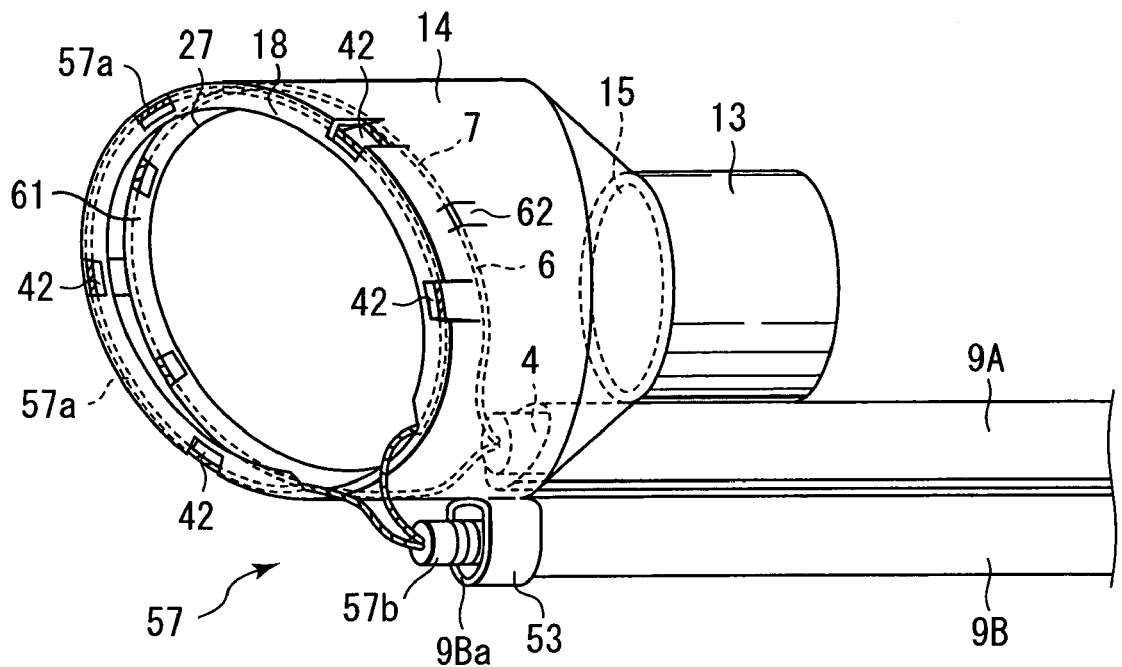
FIG. 26 is a perspective view of the structure of the main part of the endoscopic mucous membrane resection instrument according to the third embodiment of the present invention.

Further, as shown in FIG. 26, a projection portion 53, which projects outward, is provided on the outer peripheral surface of the cap section 14 in the vicinity of the communication port section 52. The projection portion 53 has a tube insertion hole 54. A distal end portion of the second tube 9B is inserted and fixed in the tube insertion hole 54. A distal opening portion 9B*a* of the second tube 9B is situated before the distal end edge of the cap section 14.

Like the second embodiment, a plurality of inwardly bent engaging portions 42 are provided at a plurality of locations along the periphery of a curved portion between the projection portion 18 formed at the distal end of the cap section 14 and the peripheral wall portion 14*a* of the cap section 14.

In the endoscopic mucous membrane resection instrument 51 of this embodiment, a diathermic snare 3 having the same structure as in the first embodiment is inserted in the first tube 9A, and a ligator 55 serving as an endoscopic treatment instrument is inserted in the second tube 9B.

The ligator 55 is provided with an elongated coil sheath 56. An operation wire 59 is inserted in the coil sheath 56, as shown in FIG. 25, so as to be advanceable/retreatable.

A ligation loop 57 is detachably provided at a distal end portion of the coil sheath 56. An operation section 58 is provided at a proximal end portion of the coil sheath 56. The ligation loop 57 includes a loop portion 57*a* formed of a resin material such as nylon in a substantially circular shape, and a tightening tube 57b formed of an elastic material such as silicone.

The operation section 58 includes a shaft-shaped guide member 58a and a slider 58b that is axially advanceable/retreatable along the guide member 58a. The guide member 58a is coupled to a proximal end portion of the coil sheath 56. Further, a wire insertion hole (not shown) for insertion of the operation wire 59 is formed in the guide member 58a.

The slider 58b has a pair of finger hook portions 58c. A proximal end portion of the operation wire 59 is connected to the slider 58b. The slider 58b is axially advanced/retreated along the guide member 58a. With the sliding operation of the slider 58b, the operation wire 59 is axially advanced/retreated for attachment/detachment of the ligation loop 57.

In the state in which the ligator 55 is attached to the endoscopic mucous membrane resection instrument 51, the ligation loop 57 is projected from the distal end of the second tube 9B, as shown in FIG. 25. In addition, as shown in FIG. 26, the loop portion 57a is circumferentially broadened along the inner periphery of the cap section 14 and is supported alternately between the projection portion 18 formed at the distal end edge of the cap section 14 and the engaging portions 42. Thereby, the loop portion 57a is held, like the loop portion 7 of the diathermic snare 3 of the first embodiment.

A restriction member 60 for restricting movement of the slider 58b is attached to the operation section 58. The restriction member 60 has the same structure as the restriction member 26 of the first embodiment. Specifically, the restriction member 60 includes projection portions 60a and a fixing portion 60b. The projection portions 60a engage the finger hook portions 58c of the slider 58b. The fixing portion 60b fixes the restriction member 60 to the guide member 58a. By attaching the restriction member 60 to the operation section 58 of the ligator 55, the ligation loop 57 disposed in the cap section 14 is locked.

As is shown in FIGS. 25 and 26, the endoscopic mucous membrane resection instrument 51 of the present embodiment has a flange-like small-diameter second projection portion 61, which is provided on the inner peripheral surface of the cap section 14. The second projection portion 61 is projected inward from the cap portion 14 near the first projection portion 18 that is provided at the distal end edge of the cap section 14, such that the second projection portion 61 and first projection portion 18 are opposed to each other at a distance. Further, second engaging portions 62, which have the same structure as the engaging portions 42, are formed at the second projection portion 61 and the peripheral wall portion 14a of the cap section 14.

In the state in which the diathermic snare 3 is attached to the endoscopic mucous membrane resection instrument 51, the distal end of the sheath 4 of diathermic snare 3 is projected into the cap section 14 from the communication port section 52, as shown in FIG. 25. In addition, as shown in FIG. 26, the snare wire 6 is fed out of the sheath 4 and circumferentially broadened along the inner periphery of the cap section 14. The snare wire 6 is supported alternately between the second projection portion 61 of the cap section 14 and the second engaging portions 62. Thereby, the snare wire 6 is held, like the loop portion 7 of the diathermic snare 3 of the first embodiment.

In the endoscopic mucous membrane resection instrument 51 of this embodiment, the loop portion 57a of the ligator 55 is disposed on the distal side of the cap section 14, and the snare wire 6 of the diathermic snare 3 is disposed on the rear side of the loop portion 57d.

Figure 27A:
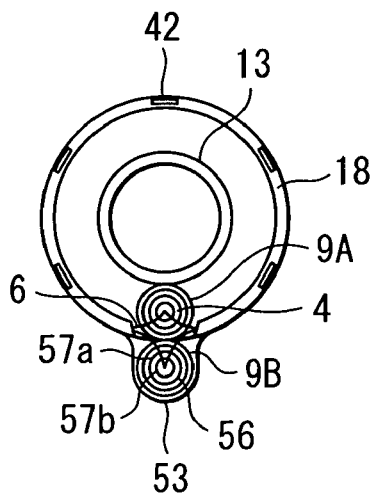
FIG. 27A is a front view of the main part, showing the state in which two flexible tubes are provided outside the endoscope attachment section of the endoscopic mucous membrane resection instrument according to the third embodiment.
Figure 27B:
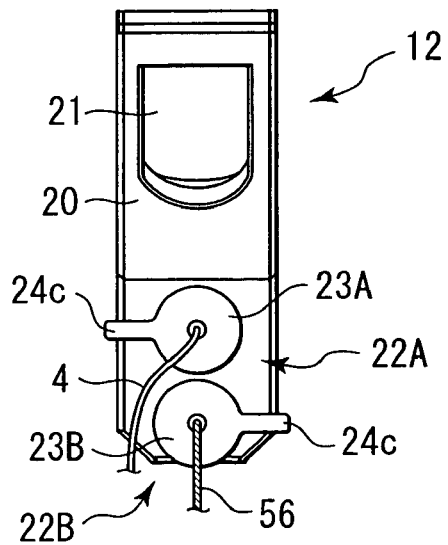
FIG. 27B is a front view of the main part, showing the state in which two treatment instrument insertion sections are vertically juxtaposed at an end portion of the hook member of the proximal-side coupling section.

As is shown in FIG. 27B, two treatment instrument insertion sections 22A and 22B are vertically juxtaposed at an end portion of the hook member 20 of the proximal-side coupling section 12. The treatment instrument insertion sections 22A and 22B are provided with treatment instrument fixing sections 23A and 23B each having the same structure as the treatment instrument fixing section 23 of the first embodiment. The sheath 4 of the diathermic snare 3 inserted in the treatment instrument insertion section 22A is detachably engaged in the treatment instrument fixing section 23A, and the coil sheath 56 of the ligator 55 inserted in the other treatment instrument insertion section 22B is detachably engaged in the treatment instrument fixing section 23B.

The operation of the endoscopic mucous membrane resection instrument 51 with the above-described structure according to the present embodiment will now be described. Specifically, referring to FIGS. 28A through 35B, a description is given of the case where a living tissue in the body, for example, a mucous membrane A1 including a target part A0, is resected using the endoscopic mucous membrane resection instrument 51 of this embodiment.

Figure 28A:
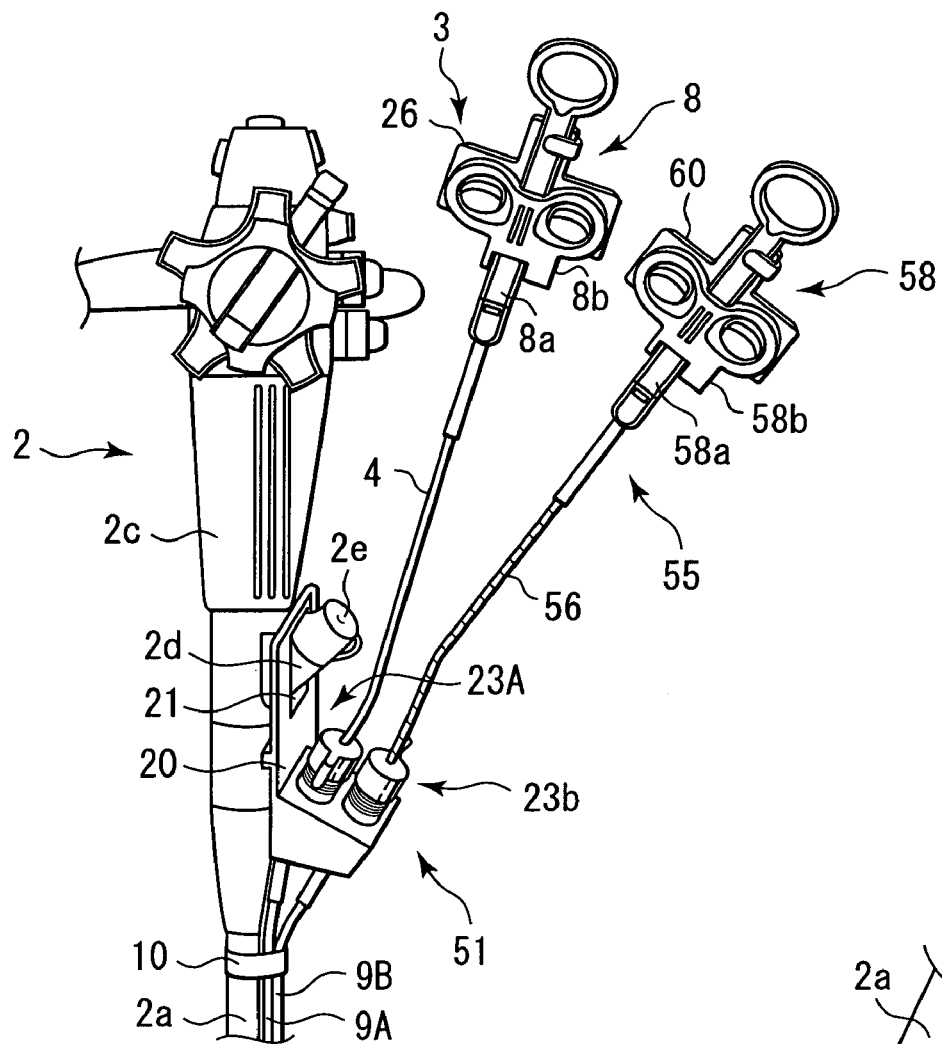
FIG. 28A is a perspective view showing a fixed state of the proximal-side coupling section of the endoscopic mucous membrane resection instrument according to the third embodiment.

Like the first embodiment, the endoscopic mucous membrane resection instrument 51 is mounted on the distal end portion 2b of the insertion section 2a of endoscope 2. At this time, as shown in FIG. 24 and FIG. 28A, the diathermic snare 3 and ligator 55 are set in the endoscopic mucous membrane resection instrument 51 in advance. In this state, the endoscopic mucous membrane resection instrument 51 is inserted into the body cavity, and the distal opening portion of the cap section 14 is moved toward a target to-be-resected mucous membrane part A2.

Figure 28B:
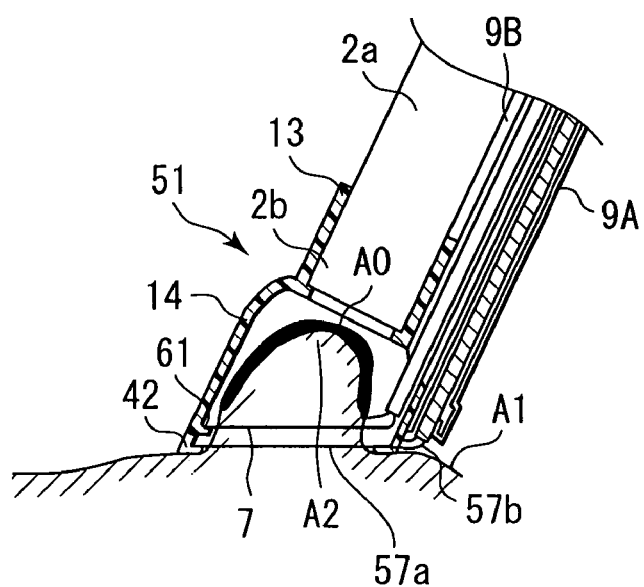
FIG. 28B is a vertical cross-sectional view of the main part, showing the state in which a to-be-resected part of the mucous membrane is raised.

Then, the distal opening portion of the cap section 14 is pushed on the mucous membrane A1. In this state, a suction force is made to act within the cap section 14 via the channel of the endoscope 2. Thereby, the mucous membrane A1 is sucked in the cap section 14, and the to-be-resected part A2 of mucous membrane A1 is raised, as shown in FIG. 28B.

Figure 29A:
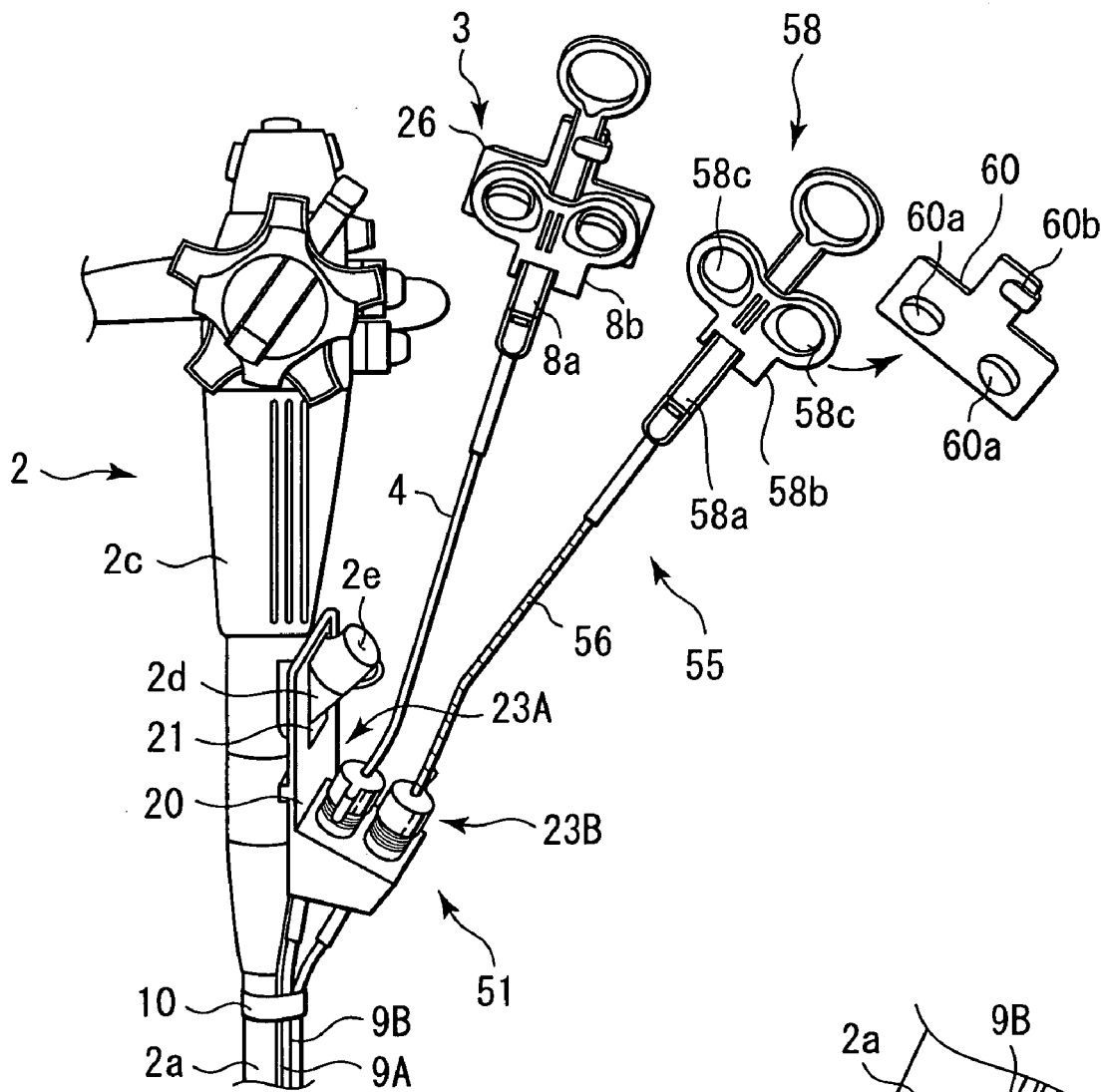
FIG. 29A is a perspective view showing the state in which a restriction member is removed from an operation section of the ligator set in the endoscopic mucous membrane resection instrument according to the third embodiment.
Figure 29B:
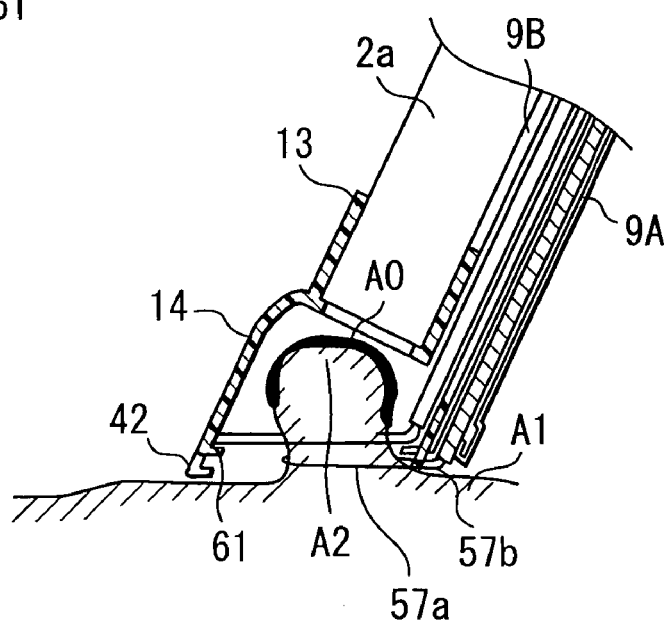
FIG. 29B is a vertical cross-sectional view of the main part, showing the state in which a loop portion of the ligator is reduced to tightly bind a proximal portion of the to-be-resected mucous membrane part.

Thereafter, as shown in FIG. 29A, the restriction member 60 is removed from the operation section 58 of the ligator 55. In this state, the slider 58b of the operation section 58 is retreated relative to the guide member 58a. By this operation, the loop portion 57a of the ligation loop 57 is disengaged from the engaging portions 42 and pulled into the coil sheath 56 via the tightening tube 57b. Thereby, as shown in FIG. 29B, the loop portion 57a of the ligation loop 57 is reduced in diameter by means of the tightening tube 57b to tightly bind a proximal portion of the to-be-resected part A2 of mucous membrane A1.

Figure 30A:
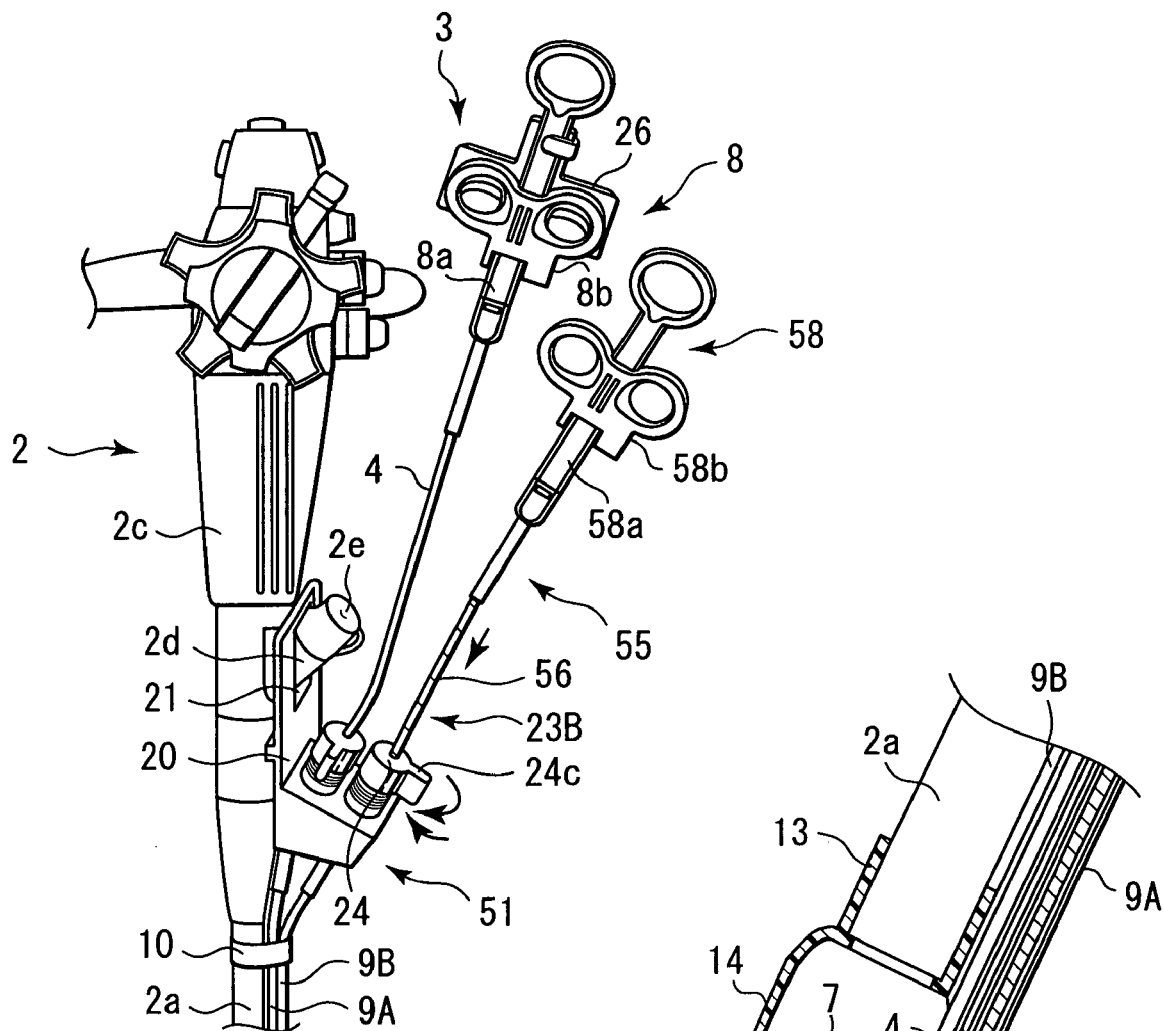
FIG. 30A is a perspective view showing the state in which the engagement of a coil sheath of the ligator of the endoscopic mucous membrane resection instrument according to the third embodiment is released.

Following the above, as shown in FIG. 30A, the knob 24c of the treatment instrument fixing section 23B is held and the rotation ring 24 is rotated to loosen the tightening of the elastic tube 25. Thereby, the engagement of the coil sheath 56 of the ligator 55 is released. In this state, the coil sheath 56 is pushed forward.

Figure 30B:
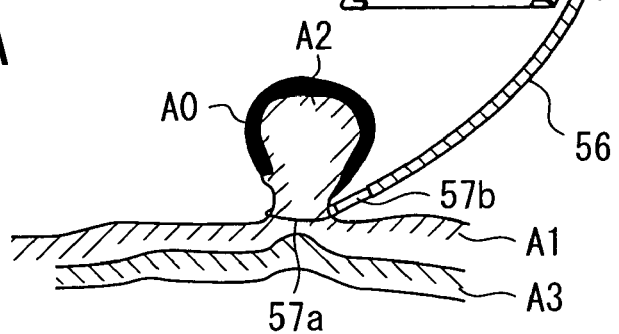
FIG. 30B is a vertical cross-sectional view of the main part, showing the state in which the distal end portion of the coil sheath is projected from the cap section.
Figures 31A, 31B:
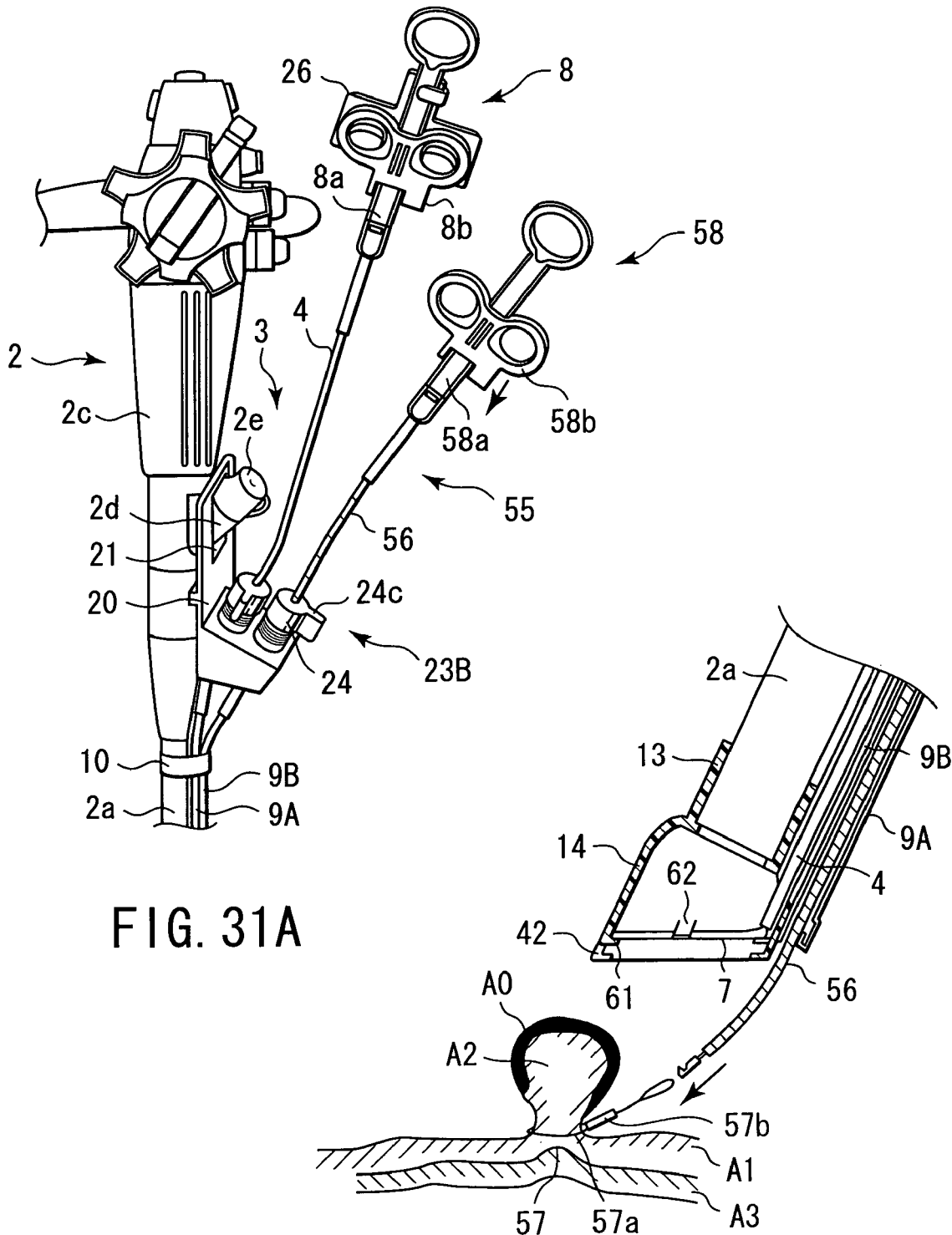
FIG. 31A is a perspective view showing the state in which the slider of the ligator of the endoscopic mucous membrane resection instrument according to the third embodiment is advanced relative to the guide member.
FIG. 31B is a vertical cross-sectional view of the main part, showing the state in which the ligation loop is released.
Figure 32A:
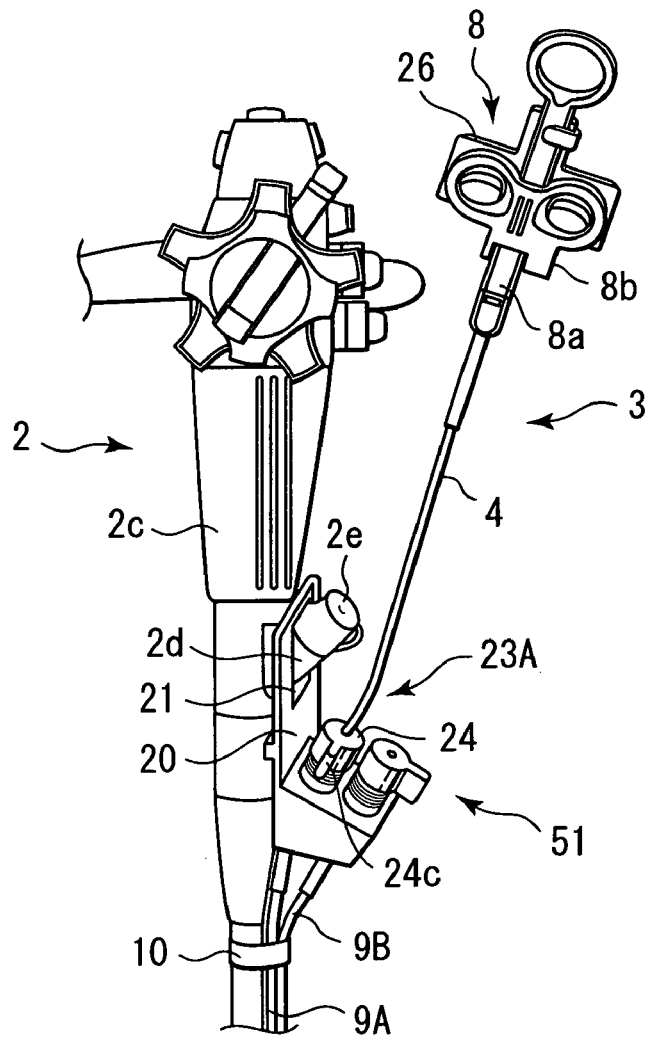
FIG. 32A is a perspective view showing the state in which the ligator is removed from the endoscopic mucous membrane resection instrument according to the third embodiment.

By the pushing operation of the coil sheath 56, as shown in FIG. 30B, the distal end portion of the coil sheath 56 is projected from the cap section 14, and the to-be-resected part A2 that is tightly bound by the ligation loop 57 is put out of the cap section 14. Subsequently, as shown in FIG. 31A, the slider 58b of the operation section 58 is advanced relative to the guide member 58a. Thereby, as shown in FIG. 31B, the operation wire 59 is projected from the coil sheath 56, and the ligation loop 57 is released. At this time, the to-be-resected part A2 is kept tightly bound by the ligation loop 57. Then, as shown in FIG. 32A, the ligator 55 is removed from the second tube 9B.

Figure 32B:
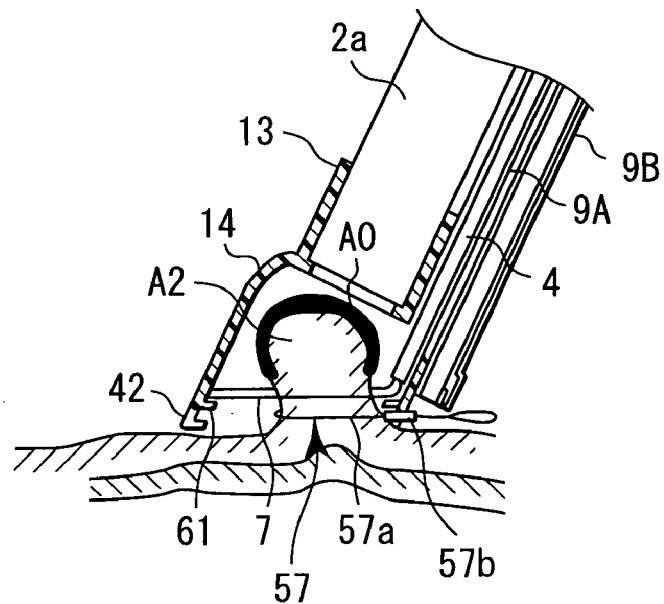
FIG. 32B is a vertical cross-sectional view of the main part, showing the state in which the to-be-resected part is sucked once again in the cap section.
Figures 33A, 33B:
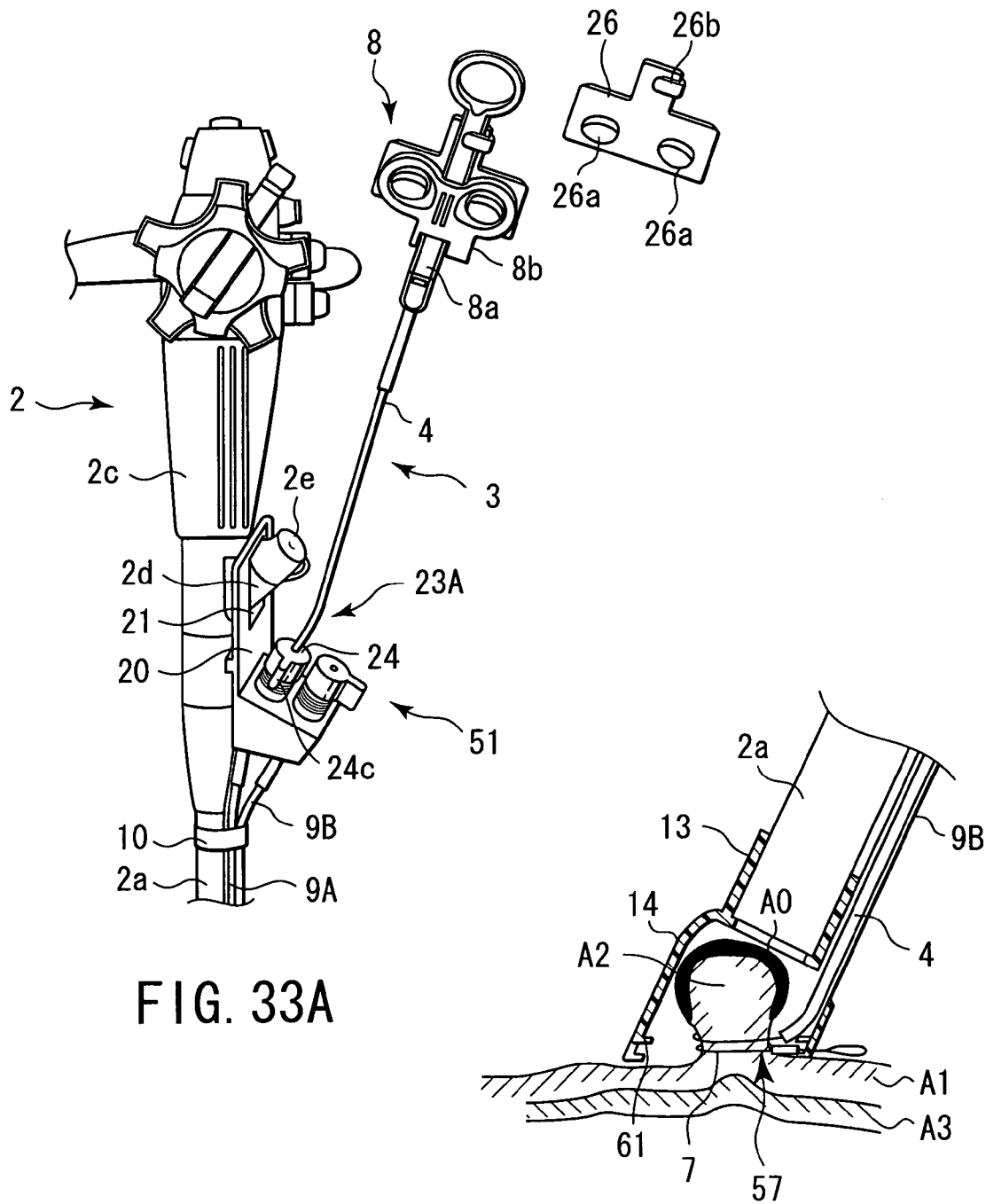
FIG. 33A is a perspective view showing the state in which a restriction member is removed from an operation section of the diathermic snare of the endoscopic mucous membrane resection instrument according to the third embodiment.
FIG. 33B is a vertical cross-sectional view of the main part, showing the state in which the to-be-resected portion in the cap section is tightly bound.

Next, as shown in FIG. 32B, the to-be-resected part A2 is sucked in the cap section 14 once again. Then, as shown in FIG. 33A, the restriction member 26 is removed from the operation section 8 of the diathermic snare 3. In this state, the slider 8b of operation section 8 is retreated relative to the guide member 8a. By this operation, the snare wire 6 is disengaged from the second engaging portions 62 and pulled into the sheath 4. Thereby, as shown in FIG. 33B, that portion of the to-be-resected part A2, which is located above the part-ligated by the ligation loop 57, is tightly bound.

Figure 34A:
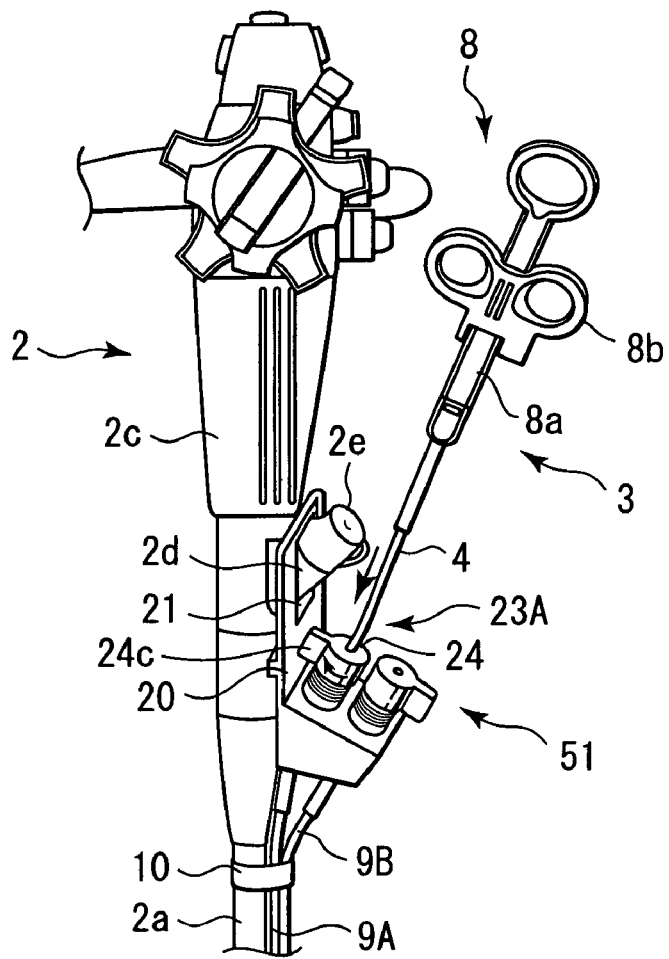
FIG. 34A is a perspective view showing the state in which the engagement of a sheath of the diathermic snare of the endoscopic mucous membrane resection instrument according to the third embodiment is released.

Following the above, as shown in FIG. 34A, the knob 24c of the treatment instrument fixing section 23A is held and the rotation ring 24 is rotated to loosen the tightening of the elastic tube 25. Thereby, the engagement of the sheath 4 of the diathermic snare 3 is released. In this state, the sheath 4 is pushed forward.

Figure 34B:
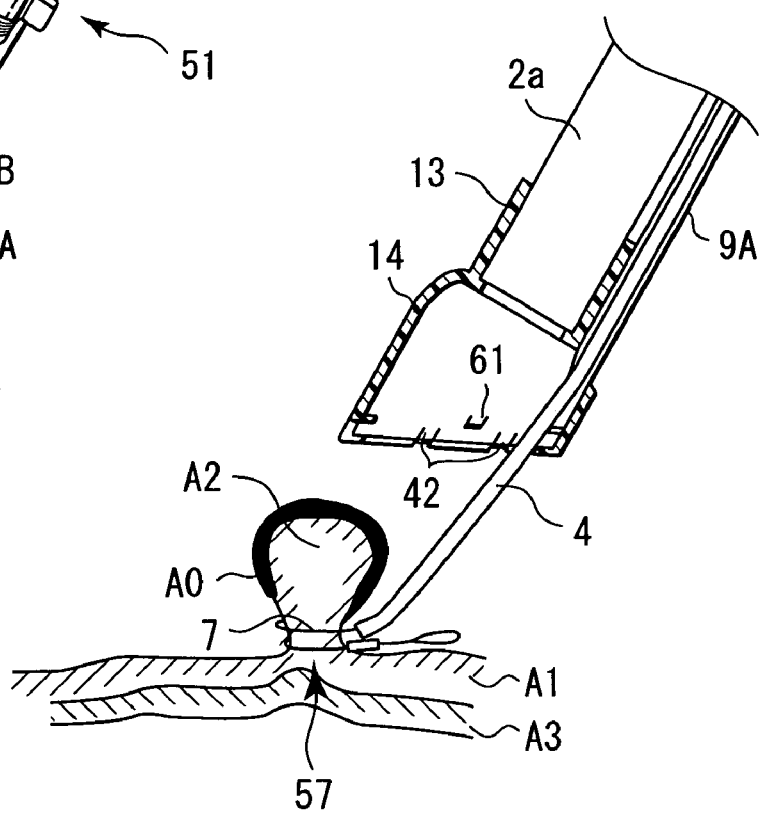
FIG. 34B is a vertical cross-sectional view of the main part, showing the state in which the distal end portion of the sheath is projected from the cap section.
Figure 35A:
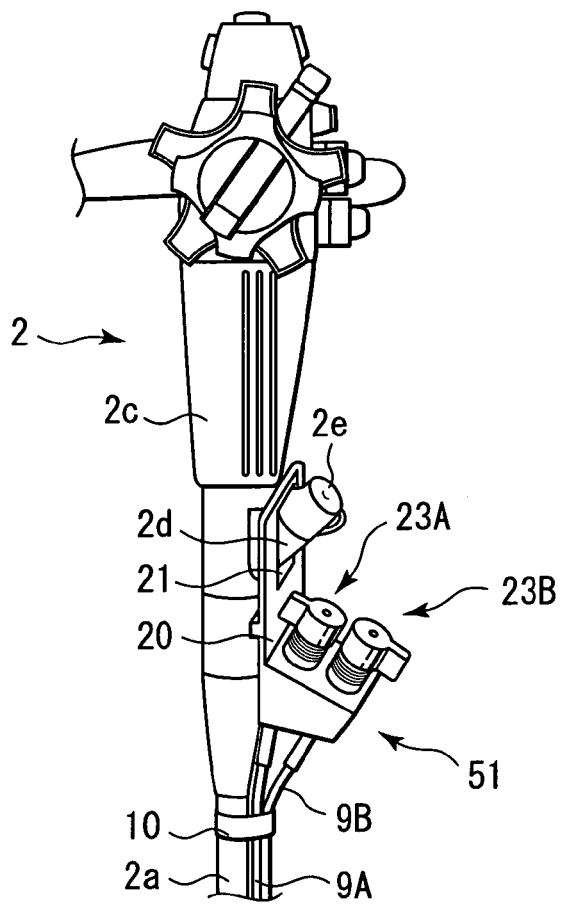
FIG. 35A is a perspective view showing the state in which the diathermic snare is removed from the endoscopic mucous membrane resection instrument according to the third embodiment.
Figure 35B:
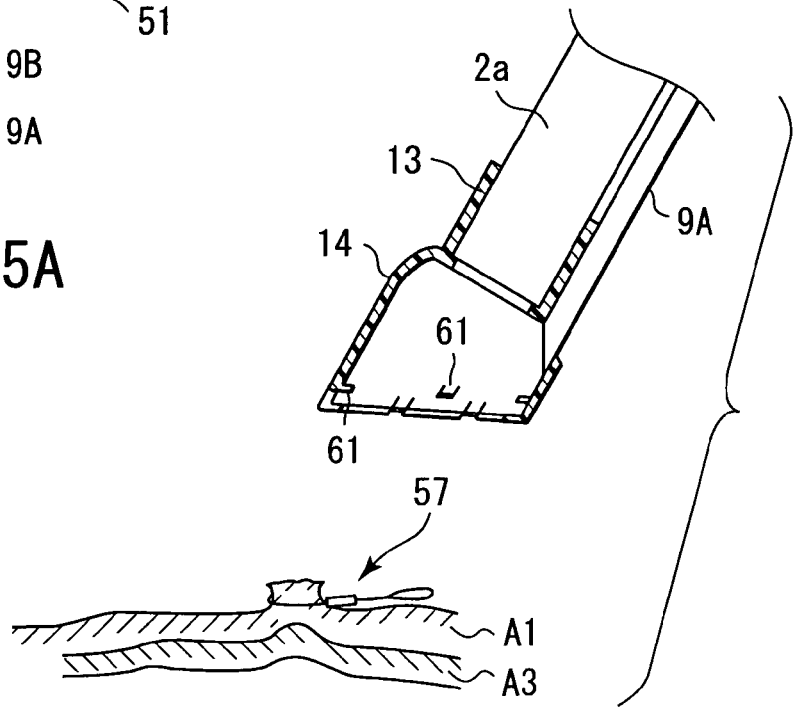
FIG. 35B is a vertical cross-sectional view of the main part, showing the completion state of the resection of the mucous membrane.

By the pushing operation of the sheath 4, as shown in FIG. 34B, the distal end portion of the sheath 4 is projected from the cap section 14 and the to-be-resected part A2 that is tightly bound by the loop portion 7 of snare wire 6 is put out of the cap section 14. Subsequently, it is confirmed using, e.g. an ultrasonic probe passed through the channel of the endoscope 2, whether the muscular layer A3 is included in the to-be-resected part A2b. Then, in the state shown in FIG. 34B, while the to-be-resected part A2 is strangulated by the loop portion 7 of snare wire 6, a high-frequency current is let to flow to the snare wire 6, thereby resecting the mucous membrane A1 of target part A0 (to-be-resected part A2).

The third embodiment with the above-described structure has the following advantages. In the endoscopic mucous membrane resection instrument 51 according to the third embodiment, the two tubes 9A and 9B are provided. The ligation loop 57 of the ligator 55 is disposed in advance on the projection portion 18 formed at the distal end of the cap section 14. The snare wire 6 of the diathermic snare 3 is disposed in advance on the inner peripheral surface of the cap section 14 near the proximal end side of the ligation loop 57. Thus, after the completion of the work for tightly binding the to-be-resected part A2 using the ligation loop 57 of the ligator 55, the work for resecting the to-be-resected part A2 can be conducted using the snare wire 6 of the diathermic snare 3 disposed in advance on the inner peripheral surface of the cap section 14 near the proximal end side of the ligation loop 57. Therefore, in this embodiment, after the work for tightly binding the to-be-resected part A2 using the ligation loop 57, it is possible to omit the looping work for setting the loop portion 7 of the snare wire 6 of the diathermic snare 3 on the inner peripheral surface of the cap section 14. It is thus possible to easily perform the endoscopic mucous membrane resection. Moreover, since hemostasis of the to-be-resected part A2 is preventatively conducted prior to resection by using the ligation loop 57, the endoscopic mucous membrane resection can be performed safely and easily.

The present invention is not limited to the above-described embodiments. For example, the endoscopic mucous membrane resection instrument 51 according to the third embodiment may be provided with two diathermic snares 3A and 3B at the same time, like the second embodiment. Thereby, the mucous membrane A1 including the relatively large target part A0 may be divided into a plurality of portions, and the divided portions may be resected by a plurality of resection operations. Besides, the endoscopic mucous membrane resection instrument 41 according to the second embodiment may be provided with the ligator 55 and diathermic snare 3 at the same time, like the third embodiment. Thereby, like the endoscopic mucous membrane resection instrument 51 of the third embodiment, after the work for tightly binding the to-be-resected part A2 using the ligation loop 57 is finished, the work for resecting the to-be-resected part A2 can be conducted using the diathermic snare 3. Furthermore, the ligator 55 and diathermic snare 3 may be successively set in the resection instrument 1 according to the first embodiment. Thereby, like the endoscopic mucous membrane resection instrument 51 of the third embodiment, after the work for tightly binding the to-be-resected part A2 using the ligation loop 57 is finished, the work for resecting the to-be-resected part A2 can be conducted using the diathermic snare 3.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic mucous membrane resection instrument comprising:

a transparent cap section detachably attached to a distal end portion of an endoscope, the cap section including a cylindrical body having a distal end and a proximal end;

a flexible tube for insertion of treatment instruments, the tube having a distal end portion and a proximal end portion, the tube being extended along an insertion section of the endoscope and the distal end portion of the tube being fixed in a state in which the distal end portion of the tube communicates with the cap section, when the cap section is attached to the endoscope;

a first endoscopic treatment instrument for a mucous membrane resection work, which has an insertion section to be removably inserted in the tube, the first treatment instrument having a first loop portion for mucous membrane resection at a distal end portion of the insertion section thereof, the first loop portion being inserted in the tube such that it is projected from the distal end of the tube;

an engagement portion which is provided at the distal end portion of the cylindrical body of the cap, the engagement portion being configured to removably fix the first treatment instrument at a first fixing position inside the cylindrical body;

a second endoscopic treatment instrument having an insertion section to be removably inserted in the tube, the second endoscopic treatment instrument being inserted in the tube when the first treatment instrument is extracted from the tube after a first mucous membrane resection work by the first endoscopic treatment instrument, thereby performing a second mucous membrane resection work, the second treatment instrument having a second loop portion for mucous membrane resection at a distal end portion of the insertion section thereof; and an abutting portion which is provided in the cylindrical body of the cap, the abutting portion being configured to introduce the second loop portion to a second fixing position inside the cylindrical body when the second treatment instrument is inserted in the tube, and the second fixing position introduced by the abutting portion being closer to the proximal end of the cylindrical body than the first fixing position.

2. The endoscopic mucous membrane resection instrument according to claim 1, wherein each of the first endoscopic treatment instrument and the second endoscopic treatment instrument is a diathermic snare in which each of the first and second loop portion is formed of a snare wire.

3. An endoscopic mucous membrane resection instrument comprising:
   a transparent cap section detachably attached to a distal end portion of an endoscope, the cap section including a cylindrical body having a distal end and a proximal end;
   first and second flexible tubes for insertion of treatment instruments, each of the first and second tubes having a distal end portion and a proximal end portion, each of the tubes being extended along an insertion section of the endoscope and the distal end portion of the tube being fixed in a state in which the distal end portion of the tube communicates with the cap section, when the cap section is attached to the endoscope;
   a first endoscopic treatment instrument for a mucous membrane resection work, which has an insertion section to be removably inserted in the first tube, the first treatment instrument having a first loop portion for mucous membrane resection at a distal end portion of the insertion section thereof, the first loop portion being inserted in the first tube such that it is projected from the distal end of the tube;
   a first engagement portion which is provided at the distal end portion of the cylindrical body of the cap, the first engagement portion being configured to removably fix the first loon portion at a first fixing position inside the cylindrical body;
   a second endoscopic treatment instrument for a mucous membrane resection work having an insertion section to be removably inserted in the second tube, the second treatment instrument having a second loop portion for mucous membrane resection at a distal end portion of the insertion section thereof; and
   a second engagement portion which is provided at the distal end portion of the cylindrical body of the cap, the second engagement portion being configured to removably fix the second loop portion at a second fixing position inside the cylindrical body, and the second fixing position at which the second loop portion is fixed by the second engagement portion being closer to the proximal end of the cylindrical body than the first fixing position.

4. The endoscopic mucous membrane resection instrument according to claim 3, wherein each of the first endoscopic treatment instrument and the second endoscopic treatment instrument is a diathermic snare in which each of the first and second loop portion is formed of a snare wire.

5. An endoscopic mucous membrane resection instrument comprising:
   a transparent cap section detachably attached to a distal end portion of an endoscope, the cap section including a cylindrical body having a distal end and a proximal end;
   first and second flexible tubes for insertion of treatment instruments, each of the first and second tubes having a distal end portion and a proximal end portion, each of the tubes being extended along an insertion section of the endoscope and the distal end portion of the tube being fixed in a state in which the distal end portion of the tube communicates with the cap section, when the cap section is attached to the endoscope;
   first and second endoscopic treatment instruments for a mucous membrane resection work having insertion sections to be removably inserted in the first and second tubes, respectively, the first and second endoscopic treatment instruments having a first and second loop portion, respectively, at a distal end portion of the insertion section thereof, the first loop portion being inserted in the first tube such that it is projected from the distal end of the first tube;
   a first engagement portion which is provided at the distal end portion of the cylindrical body of the cap, the first engagement portion being configured to removably fix the first loop portion at a first fixing position inside the cylindrical body;
   a second engagement portion which is provided at the distal end portion of the cylindrical body of the cap, the second engagement portion being configured to removably fix the second loop portion at a second fixing position inside the cylindrical body, and the second fixing position at which the second loop portion is fixed by the second engagement portion being closer to the proximal end of the cylindrical body than the first fixing position.

6. The endoscopic mucous membrane resection instrument according to claim 5, wherein the first endoscopic treatment instrument includes a ligator in which the first loop portion is formed of a ligation loop capable of tightly binding and ligating a living tissue, and
   the second endoscopic treatment instrument is a diathermic snare in which the second loop portion is formed of a snare wire.

7. An endoscopic mucous membrane resection method comprising:
   a resection instrument setting step of fitting an endoscopic mucous membrane resection instrument on a distal end portion of an insertion section of an endoscope, the endoscopic mucous membrane resection instrument being set in a state in which a first diathermic snare is preset in a cap section such that a first loop portion of the first diathermic snare is is removably fixed at a first fixing position inside a cylindrical body of the cap section;
   a step of inserting the endoscope and the resection instrument into a body cavity and moving a distal opening portion of the cap section toward a target to-be-resected mucous membrane;
   a step of causing a suction force to act within the cap section in a state in which the distal opening portion of the cap section is pushed on the mucous membrane, thereby sucking and raising a to-be-resected part of the mucous membrane within the cap section by a negative pressure;
   a step of reducing a size of the first loop portion of a snare wire of the first diathermic snare by operating the first diathermic snare, thereby tightly binding a proximal portion of a raised part of the mucous membrane;
   a first mucous membrane resection work step of causing a high-frequency current to flow in the snare wire while strangulating the proximal portion of the raised part by the first loop portion of the snare wire, thereby resecting the to-be-resected part of the mucous membrane;
   a step of removing the first diathermic snare used in the preceding steps from the resection instrument after the completion of the first mucous membrane resection work; and a second resection work step of resecting a remaining part of the mucous membrane, which is not resected by the first resection work, the second resection work step including:

a step of moving the distal opening portion of the cap section toward a second to-be-resected part of the target mucous membrane in a state in which the first diathermic snare is not set in the resection instrument;

a step of causing a suction force to act within the cap section in a state in which the distal opening portion of the cap section is pushed on the second to-be-resected part of the mucous membrane, thereby sucking and raising the second to-be-resected part of the mucous membrane within the cap section by a negative pressure;

a step of introducing a second loop portion of a second diathermic snare at a second fixing position inside the cylindrical body of the cap section, the second fixing position being closer to a proximal end of the cylindrical body of the cap section than the first fixing position;

a step of largely raising the second to-be-resected part of the mucous membrane by sucking the second to-be-resected part more strongly than before insertion of the second diathermic snare;

a step of reducing a size of the second loop portion of a snare wire of the second diathermic snare by operating the second diathermic snare, thereby tightly binding a proximal portion of the second to-be-resected part of the mucous membrane;

a second resection work step of causing, like the first resection work, a high-frequency current to flow in the snare wire while strangulating the proximal portion of the to-be-resected part by the second loop portion of the snare wire, thereby resecting the remaining to-be-resected part; and a recovery step of recovering, after the completion of the second resection work, the resected part of the mucous membrane resected by the second resection work and the resected part of the mucous membrane resected by the first resection work in the state in which both the resected parts are sucked and held in the cap section, by taking out both the resected parts from the body cavity along with the endoscope.

8. An endoscopic mucous membrane resection method comprising:

a resection instrument setting step of fitting an endoscopic mucous membrane resection instrument on a distal end portion of an insertion section of an endoscope, the endoscopic mucous membrane resection instrument being set in a state in which first and second diathermic snares are preset in a cap section such that first and second loop portions, respectively, of the first and second diathermic snares are removably fixed at first and second fixing positions, respectively, positioned inside a cylindrical body of the cap section, the second fixing position being closer to a proximal end of the cylindrical body of the cap section than the first fixing position;

a step of inserting the endoscope and the resection instrument into a body cavity and moving a distal opening portion of the cap section toward a target to-be-resected mucous membrane;

a step of causing a suction force to act within the cap section in a state in which the distal opening portion of the cap section is pushed on the mucous membrane, thereby sucking and raising a to-be-resected part of the mucous membrane within the cap section by a negative pressure;

a step of reducing a size of the first loop portion of the first diathermic snare, thereby tightly binding a proximal portion of a raised part of the mucous membrane;

a first mucous membrane resection work step of causing a high-frequency current to flow in the first loop portion while strangulating the proximal portion of the raised part by the first loop portion of the first diathermic snare, thereby resecting the to-be-resected part of the mucous membrane;

a step of removing the first diathermic snare used in the preceding steps from the resection instrument after the completion of the first mucous membrane resection work; and a second resection work step of resecting a remaining part of the mucous membrane, which is not resected by the first resection work, the second resection work step including:

a step of moving the distal opening portion of the cap section toward a second to-be-resected part of the target mucous membrane;

a step of causing a suction force to act within the cap section in a state in which the distal opening portion of the cap section is pushed on the second to-be-resected part of the mucous membrane, thereby sucking and raising the second to-be-resected part of the mucous membrane within the cap section by a negative pressure;

a step of tightly binding a proximal portion of a raised part of the mucous membrane by the second loop portion of the second diathermic snare;

a second resection work step of causing a high-frequency current to flow in the second loop portion while strangulating the proximal portion of the raised part by the second loop portion of the second diathermic snare, thereby resecting the remaining to-be-resected part; and a recovery step of recovering, after the completion of the second resection work, the resected part of the mucous membrane resected by the second resection work and the resected part of the mucous membrane resected by the first resection work in the state in which both the resected parts are sucked and held in the cap section, by taking out both the resected parts from the body cavity along with the endoscope.

9. An endoscopic mucous membrane resection method comprising:

a resection instrument setting step of fitting an endoscopic mucous membrane resection instrument on a distal end portion of an insertion section of an endoscope, the endoscopic mucous membrane resection instrument including a transparent cap section detachably attached to the distal end portion of the endoscope, one diathermic snare and one ligator, the endoscopic mucous membrane resection instrument being set in a state in which a loop portion of the ligator is removably fixed at a first fixing position inside a cylindrical body of the cap section and a loop portion of the diathermic snare is removably fixed at a second fixing position inside the cylindrical body of the cap section, the second fixing position being closer to a proximal end of the cylindrical body of the cap than the first fixing position;

a step of inserting the endoscope and the resection instrument into a body cavity and moving a distal opening portion of the cap section toward a target to-be-resected mucous membrane;

a step of causing a suction force to act within the cap section in a state in which the distal opening portion of the cap section is pushed on the mucous membrane, thereby sucking and raising a to-be-resected part of the mucous membrane within the cap section by a negative pressure;

a step of reducing a size of the loop portion of the ligator by operating the ligator, thereby tightly binding a proximal portion of a raised part of the mucous membrane;

a step of releasing the loop portion of the ligator and keeping a state in which the proximal portion of the raised part of the mucous membrane is tightly bound by the loop portion of the ligator;

a step of sucking in the cap section the raised part of the mucous membrane tightly bound by the loop portion of the ligator;

a step of reducing a size of the loop portion of a the diathermic snare by operating the diathermic snare, thereby tightly binding an upper-side portion of the raised part of the mucous membrane that is already tightly bound by the loop portion of the ligator;

a resection work step of causing a high-frequency current to flow in the loop portion of the diathermic snare while strangulating the upper-side portion of the raised part of the mucous membrane by the loop portion of the diathermic snare, thereby resecting the to-b e-resected part of the mucous membrane; and a recovery step of recovering, after the completion of the resection work, the resected part of the mucous membrane resected by the resection work in a state in which the resected part is sucked and held in the cap section, by taking out the resected part from the body cavity along with the endoscope.

\* \* \* \* \*